US010457743B2

(12) United States Patent
Thorn Clausen et al.

(10) Patent No.: US 10,457,743 B2
(45) Date of Patent: Oct. 29, 2019

(54) ANTIBODIES RECOGNIZING THE N-TERMINAL PART OF TISSUE FACTOR PATHWAY INHIBITOR CAPABLE OF ELICITING PRO-COAGULANT ACTIVITY

(71) Applicant: Novo Nordisk A/S, Bagsvaerd (DK)

(72) Inventors: Jes Thorn Clausen, Hoeng (DK); Berit Olsen Krogh, Roedovre (DK); Helle Heibroch Petersen, Koebenhavn V (DK); Cecilia Augustsson, Malmoe (DK)

(73) Assignee: Novo Nordisk A/S, Bagsvaerd (DK)

( * ) Notice: Subject to any disclaimer, the term of this patent is extended or adjusted under 35 U.S.C. 154(b) by 514 days.

(21) Appl. No.: 14/905,461

(22) PCT Filed: Jul. 18, 2014

(86) PCT No.: PCT/EP2014/065491
§ 371 (c)(1),
(2) Date: Jan. 15, 2016

(87) PCT Pub. No.: WO2015/007880
PCT Pub. Date: Jan. 22, 2015

(65) Prior Publication Data
US 2016/0152729 A1    Jun. 2, 2016

Related U.S. Application Data

(60) Provisional application No. 61/856,869, filed on Jul. 22, 2013.

(30) Foreign Application Priority Data

Jul. 19, 2013  (EP) .................................... 13177184
Mar. 14, 2014  (EP) .................................... 14159679

(51) Int. Cl.
A61K 39/395    (2006.01)
C07K 16/38     (2006.01)
A61K 39/00     (2006.01)

(52) U.S. Cl.
CPC ........ *C07K 16/38* (2013.01); *A61K 2039/505* (2013.01); *C07K 2299/00* (2013.01); *C07K 2317/30* (2013.01); *C07K 2317/34* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 5,369,038 A  *  11/1994  Koike ................... C07K 16/38
                                                            435/7.1
8,252,913 B2      8/2012   Schaub et al.
9,228,022 B2      1/2016   Hilden et al.
9,896,513 B2  *   2/2018   Krogh .................. C07K 16/468
2012/0017288 A1   1/2012   Riesbeck et al.
2012/0028901 A1   2/2012   Dockal et al.

FOREIGN PATENT DOCUMENTS

| CN | 103080135 A | 5/2013 | |
| EP | 539975 A1 | 5/1993 | |
| WO | 2006/122139 A2 | 11/2006 | |
| WO | WO-2010017196 A2 * | 2/2010 | ......... A61K 39/3955 |
| WO | 2010072687 A1 | 7/2010 | |
| WO | 2010072691 A1 | 7/2010 | |
| WO | 2012135671 A2 | 10/2012 | |
| WO | WO-2012135671 A2 * | 10/2012 | ............. C07K 16/38 |
| WO | WO-2014140240 A1 * | 9/2014 | ............. C07K 16/38 |

OTHER PUBLICATIONS

Harlow et al., Antibodies, A Laboratory Manual, Cold Spring Harbor Laboratory, 1988, p. 76).*
Janeway et al., Immunobiology, 3rd edition, 1997, Garland Press, pp. 3:1-3:11.*
Rudikoff et al., Proc Natl Acad Sci USA, 1982, 79:1979-1983.*
"Anti-human TFPI (Kunitz-1)" Art No. MW1846. url <http://www.sanquin.nl/repository/reagentia/ifu/MW1846.pdf> Accessed Nov. 19, 2015.
"Anti-TFPI antibody :: Mouse TFPI Monoclonal Antibody" Catalog #MBS 532510 url <http://www.mybiosource.com/prods/Antibody/Monoclonal/TFPI/datasheet.php?products_id=532510> Accessed Nov. 19, 2015. Augustsson et al., "Differential effects on TFPI levels upon exposure of human endothelial cells and cynomolgus monkey vascular beds to TFPI KPI-2 antibody mAb 2021 and TFPI KPI-3 antibody mAb 0001" J Thromb Haemost. 2013, 11:s2, Abstract PA 4.14-2 p. 477.
Baugh et al., "Regulation of Extrinsic Pathway Factor Xa Formation by Tissue Factor Pathway Inhibitor"Journal of Biological Chemistry 1998 vol. 273(8) pp. 4378-86.
Dockal, Michael et al. "Peptides Binding to Kunitz Domain 1 of Tissue Factor Pathway Inhibitor (TFPI) Inhibit All Functions of TFPI and Improve Thrombin Generation of Hemophilia Plasma" 53rd ASH Annual Meeting and Exposition. 2011.
Dockal, Michael et al. "Peptides Inhibiting Tissue Factor Pathway Inhibitor Improve Hemostasis in Mice" 53rd ASH Annual Meeting and Exposition. 2011.
Girard et al., "Functional significance of the Kunitz-type inhibitory domains of lipoprotein-associated coagulation inhibitor" Nature 1989 vol. 338(6215) pp. 518-520.
Horie, S et al. "Oxidized low-density lipoprotein impairs the anti-coagulant function of tissue-factor-pathway inhibitor through oxidative modification by its high association and accelerated degradation in cultured human endothelial cells." Biochemical Jornal. 2000. vol. 352(2) pp. 277-285.

(Continued)

*Primary Examiner* — Michael Szperka
(74) *Attorney, Agent, or Firm* — Rosmarie R. Wilk-Orescan

(57) ABSTRACT

The present invention relates to an antibody that specifically binds to an epitope in the N-terminal part (residues 1 to 79) of tissue factor pathway inhibitor (TFPI). An antibody according to the invention may be capable of neutralising TFPI inhibition of the TF/FVIIa complex, even in the presence of elevated levels of TFPI. Such antibodies may find utility in the treatment of subjects with a coagulopathy, such as those with haemophilia A or B, with or without inhibitors.

Figure 1:
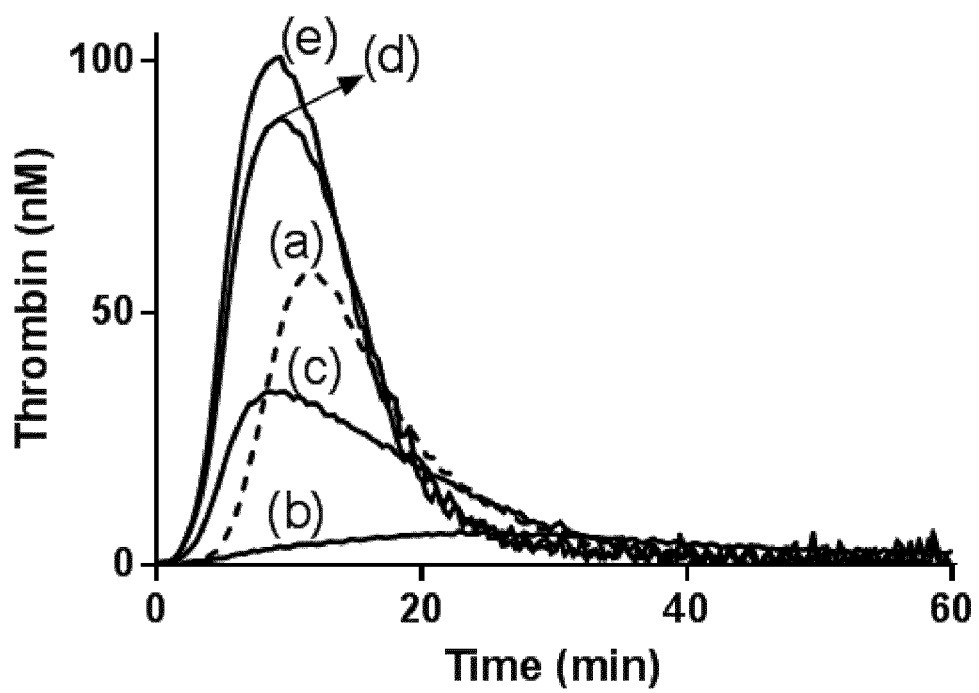

10 Claims, 2 Drawing Sheets
Specification includes a Sequence Listing.

(56) References Cited

OTHER PUBLICATIONS

Mast et al. "Characterization of the Association of Tissue Factor Pathway Inhibitor With Human Placenta" Arteriosclerosis, Thrombosis and Vascular Biology. 2002 vol. 22 pp. 2099-2104.
Peraramelli et al., "The Kunitz 1 and Kunitz 3 domains of tissue factor pathway inhibitor are required for efficient inhibition of factor Xa" Thrombosis and Haemostasis. 2012 vol. 108(2) pp. 266-276.
Tiemann, Carsten et al. "Detection of the three Kunitz-type single domains of membrane-bound tissue factor pathway inhibitor (TFPI) by flow cytometry." European Journal of Clinical Chemistry and Clinical Biochemistry 1997 vol. 35(11) pp. 855-860.
Petersen Lars C, "Hemostatic properties of a TFPI antibody," Thrombosis Research, 2012, vol. 129, No. Suppl. 2, pp. S44-S45.

\* cited by examiner

SEQUENCE LISTING

<160> NUMBER OF SEQ ID NOS: 20

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Asn Ile Phe Thr
        35                  40                  45

Arg Gln Cys Glu Glu Phe Ile Tyr Gly Gly Cys Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
        210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275

<210> SEQ ID NO 2
<211> LENGTH: 79
<212> TYPE: PRT
<213> ORGANISM: Homo sapiens

<400> SEQUENCE: 2

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Asn Ile Phe Thr
                35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp
 65                  70                  75

<210> SEQ ID NO 3
<211> LENGTH: 161
<212> TYPE: PRT
<213> ORGANISM: Homo sapiens

<400> SEQUENCE: 3

Asp Ser Glu Glu Asp Glu Glu His Thr Ile Ile Thr Asp Thr Glu Leu
 1               5                  10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Asn Ile Phe Thr
                35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
                115                 120                 125

Gly Cys Leu Gly Asn Met Asn Asn Phe Glu Thr Leu Glu Glu Cys Lys
                130                 135                 140

Asn Ile Cys Glu Asp Gly Pro Asn Gly Phe Gln Val Asp Asn Tyr Gly
 145                 150                 155                 160

Thr

<210> SEQ ID NO 4
<211> LENGTH: 121
<212> TYPE: PRT
<213> ORGANISM: Mus musculus

<400> SEQUENCE: 4

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Ser Ser Tyr
                20                  25                  30

Gly Val His Trp Val Arg Gln Ser Pro Gly Lys Gly Leu Glu Trp Leu
                35                  40                  45

Gly Val Ile Trp Arg Gly Gly Ser Thr Asp Phe Asn Ala Ala Phe Met
                50                  55                  60

Ser Arg Val Ser Phe Thr Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                85                  90                  95

```
Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 5
<211> LENGTH: 107
<212> TYPE: PRT
<213> ORGANISM: Mus musculus

<400> SEQUENCE: 5

Asp Ile Val Met Thr Gln Ser Gln Lys Phe Met Ser Thr Thr Val Gly
1               5                   10                  15

Asp Lys Val Ser Ile Pro Cys Lys Ala Ser Glu Asn Val Gly Ala Ala
            20                  25                  30

Val Ala Trp Tyr Gln Gln Lys Pro Gly Gln Ser Pro Thr Leu Leu Ile
        35                  40                  45

Tyr Ser Ala Ser Asn Arg Tyr Thr Gly Ile Pro Asp Arg Phe Thr Gly
    50                  55                  60

Ser Gly Ser Gly Thr Asp Phe Thr Leu Thr Ile Arg Thr Val Gln Ser
65                  70                  75                  80

Glu Asp Leu Ala Asp Tyr Phe Cys Gln Gln Tyr Thr Asn Tyr Pro Thr
                85                  90                  95

Phe Gly Gly Gly Thr Lys Leu Glu Ile Lys Arg
            100                 105

<210> SEQ ID NO 6
<211> LENGTH: 121
<212> TYPE: PRT
<213> ORGANISM: Mus musculus

<400> SEQUENCE: 6

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 7
<211> LENGTH: 107
<212> TYPE: PRT
<213> ORGANISM: Mus musculus
```

-continued

<400> SEQUENCE: 7

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg
            100                 105

<210> SEQ ID NO 8
<211> LENGTH: 121
<212> TYPE: PRT
<213> ORGANISM: Mus musculus

<400> SEQUENCE: 8

Gln Val Gln Leu Lys Gln Ser Gly Pro Gly Leu Val Gln Pro Ser Gln
1               5                   10                  15

Ser Leu Ser Ile Ser Cys Thr Val Ser Gly Phe Ser Leu Thr Gly Tyr
                20                  25                  30

Gly Val His Trp Ile Arg Gln Ser Pro Gly Lys Gly Leu Glu Trp Leu
            35                  40                  45

Gly Val Ile Trp Arg Gly Gly Ser Ile Asp Tyr Asn Ala Ala Phe Met
50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 9
<211> LENGTH: 107
<212> TYPE: PRT
<213> ORGANISM: Mus musculus

<400> SEQUENCE: 9

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Glu Leu Leu Ile
            35                  40                  45

Tyr Ser Ala Ser Asn Arg Tyr Thr Arg Val Pro Asp Arg Phe Thr Gly
50                  55                  60

-continued

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg
            100                 105

<210> SEQ ID NO 10
<211> LENGTH: 115
<212> TYPE: PRT
<213> ORGANISM: Mus musculus

<400> SEQUENCE: 10

Asp Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Trp Ala Tyr Asp Gly Pro Trp Gly Gln Gly Thr Leu Val Thr
            100                 105                 110

Val Ser Ala
        115

<210> SEQ ID NO 11
<211> LENGTH: 107
<212> TYPE: PRT
<213> ORGANISM: Mus musculus

<400> SEQUENCE: 11

Gln Ile Val Leu Ser Gln Ser Pro Ala Leu Leu Ser Ala Ser Pro Gly
1               5                   10                  15

Glu Lys Val Thr Met Thr Cys Arg Ala Ser Ser Ser Val Ser His Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg
            100                 105

<210> SEQ ID NO 12
<211> LENGTH: 116
<212> TYPE: PRT
<213> ORGANISM: Mus musculus

<400> SEQUENCE: 12

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asn Thr Ile Phe Asp Pro Lys Phe
    50                  55                  60

Gln Gly Arg Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Gly Arg Trp Tyr Ala Met Asp Tyr Trp Gly Gln Gly Thr Ser Val
            100                 105                 110

Thr Val Ser Ser
            115

<210> SEQ ID NO 13
<211> LENGTH: 113
<212> TYPE: PRT
<213> ORGANISM: Mus musculus

<400> SEQUENCE: 13

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr His Phe Pro Trp Thr Phe Gly Gly Gly Thr Lys Leu Glu Ile Lys
            100                 105                 110

Arg

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14
cccttgacca ggcatcccag                                              20

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
gctctagact aacactcatt cctgttgaag ctcttg        36

<210> SEQ ID NO 16
<211> LENGTH: 222
<212> TYPE: PRT
<213> ORGANISM: mus musculus

<400> SEQUENCE: 16

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys
    210                 215                 220

<210> SEQ ID NO 17
<211> LENGTH: 213
<212> TYPE: PRT
<213> ORGANISM: mus musculus

<400> SEQUENCE: 17

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

```
Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 18
<211> LENGTH: 86
<212> TYPE: PRT
<213> ORGANISM: Artificial
<220> FEATURE:
<223> OTHER INFORMATION: Tagged TFPI fragment

<400> SEQUENCE: 18

Gly Ser Ser Gly Ser Ser Gly Asp Ser Glu Glu Asp Glu Glu His Thr
1               5                   10                  15

Ile Ile Thr Asp Thr Glu Leu Pro Pro Leu Lys Leu Met His Ser Phe
            20                  25                  30

Cys Ala Phe Lys Ala Asp Asp Gly Pro Cys Lys Ala Ile Met Lys Arg
        35                  40                  45

Phe Phe Phe Asn Ile Phe Thr Arg Gln Cys Glu Glu Phe Ile Tyr Gly
50                  55                  60

Gly Cys Glu Gly Asn Gln Asn Arg Phe Glu Ser Leu Glu Glu Cys Lys
65                  70                  75                  80

Lys Met Cys Thr Arg Asp
            85
```

```
<210> SEQ ID NO 19
<211> LENGTH: 448
<212> TYPE: PRT
<213> ORGANISM: Artificial Sequence
<220> FEATURE:
<223> OTHER INFORMATION: Synthetic

<400> SEQUENCE: 19

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80
```

```
Lys Met Asn Ser Leu Gln Ala Asp Asp Thr Ala Ile Tyr Tyr Cys Ala
                85                  90                  95
Lys Asn Ser His Gly Asn Tyr Val Gly Tyr Ala Met Asp Tyr Trp Gly
            100                 105                 110
Gln Gly Thr Ser Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445
```

<210> SEQ ID NO 20
<211> LENGTH: 227
<212> TYPE: PRT
<213> ORGANISM: Artificial Sequence
<220> FEATURE:
<223> OTHER INFORMATION: Synthetic

```
<400> SEQUENCE: 20

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys
225
```

ANTIBODIES RECOGNIZING THE N-TERMINAL PART OF TISSUE FACTOR PATHWAY INHIBITOR CAPABLE OF ELICITING PRO-COAGULANT ACTIVITY

CROSS-REFERENCE TO RELATED APPLICATIONS

This application is a 35 U.S.C. § 371 National Stage application of International Application PCT/EP2014/065491 (WO 2015/007880), filed Jul. 18, 2014, which claims priority to European Patent Applications 13177184.2, filed Jul. 19, 2013 and 14159679.1, filed Mar. 14, 2014; this application claims priority under 35 U.S.C. § 119 to U.S. Provisional Application 61/856,869; filed Jul. 22, 2013, the contents thereof which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 13, 2016, is named 8712US02_SeqList.txt and is 26 kilobytes in size.

FIELD OF THE INVENTION

The present invention relates to pro-coagulant antibodies, and compositions thereof, that are capable of specifically binding to an epitope in the N-terminal part of tissue factor pathway inhibitor (TFPI). The invention also relates to the pharmaceutical and therapeutic uses of such antibodies.

BACKGROUND

In the bleeding individual, coagulation is initiated by the Tissue Factor (TF)/activated Factor VII (FVIIa) complex when extravascular TF is exposed to FVIIa in the blood. TF/FVIIa complex formation leads to the activation of Factor X (FX) to FXa which, together with activated Factor V (FVa), generates a limited amount of thrombin. The initial amount of thrombin activates platelets which, in turn, result in the surface exposure of platelet phospholipids that support the assembly and binding of the tenase complex, consisting of activated Factor VIII (FVIIIa) and activated Factor IX (FIXa). The tenase complex is a very efficient catalyst of FX activation and FXa generated in this step serves as the active protease in the FVa/FXa pro-thrombinase complex which is responsible for the final thrombin burst. Thrombin cleaves fibrinogen to generate fibrin monomers, which polymerise to form a fibrin network. The rapid and extensive thrombin burst is a prerequisite for the formation of a solid and stable fibrin clot.

An inadequate propagation of FXa and thrombin generation caused by FVIII or FIX deficiency is the underlying reason for the bleeding diathesis in haemophilia A or B patients, respectively. In people with haemophilia, FXa generation is primarily driven by the TF/FVIIa complex: FVIII or FIX deficiency leads to rudimentary FXa generation by the tenase complex. TF/FVIIa-mediated activation of FX to FXa is, however, temporary because tissue factor pathway inhibitor (TFPI) inhibits the TF/FVIIa complex in an auto-regulatory loop. Feed-back inhibition leads to formation of the TF/FVIIa/FXa/TFPI complex. Blunting of TFPI inhibition prolongs TF/FVIIa-mediated activation of FX during initiation of coagulation and promotes haemostasis. Haemophilia patients suffer from an impaired tenase activity due to, e.g., FVIII or FIX deficiency. Blocking of TFPI inhibition can in these patients compensate for an inadequate FXa generation and normalize the bleeding diathesis.

TFPI is a slow, tight-binding competitive inhibitor which regulates FX activation through inhibition of both FXa and the TF/FVIIa complex. TFPI contains three tandemly arranged Kunitz-type Protease Inhibitor domains (KPI 1-3). TFPI inhibition of FXa occurs in a biphasic reaction which initially leads to a loose TFPI-FXa complex, which then slowly rearranges into a tight binding TFPI-FXa complex, where KPI-2 binds and blocks the active site of FXa. Following initiation of coagulation, TF/FVIIa-mediated FXa generation is tightly down-regulated by TFPI. TF/FVIIa is inhibited by TFPI in a process which, as a rate limiting step, appears to involve TFPI inhibition of FXa, either when FXa is bound to the TF/FVIIa complex or bound in the near vicinity of the TF/FVIIa complex on the cell membrane (Baugh et al., *J Biol Chem.* 1998; 273(8):4378-86). KPI-1 contributes to the formation of the tight TFPI-FXa complex and directly binds and also blocks the active site of TF-bound FVIIa (Girard et al., *Nature* 1989; 338:518-520; Peraramelli et al., *Thromb. Haemost.* 2012; 108:266-276).

In vivo, TFPI is found in several cellular compartments. A major fraction of TFPI is associated with the vascular endothelium and a minor fraction circulates in the blood. Two splice variants of TFPI, TFPI alpha (TFPIα) and TFPI beta (TFPIβ), have been described to be present in humans. Endothelial cells are the major sites for TFPI production and express both variants. The predominant form on the endothelial cell surface is presumably TFPIβ. TFPIα is either secreted into the plasma or found in intracellular stores, which can be released upon certain stimuli. Secreted TFPIα circulates in the blood either as a full-length protein (10%) or as modified proteins with different molecular masses (90%); the latter may be due to, e.g., truncation of the C-terminal region or association with lipoproteins. Secreted TFPIα may also bind to the endothelial cells surface through interactions with e.g. glycoaminoglycans. TFPIα is also produced by and stored in platelets.

The half-life of TFPI in humans is known to be about 60-120 minutes and the total normal human plasma TFPI concentration is known to be about 1.0-2.5 nM. In contrast, the half-life of antibodies in humans is known to be long: up to several weeks, depending on the immunoglobulin subtype, origin and specific amino acid composition. The total TFPI concentration (free TFPI plus TFPI/antibody complexes) in plasma may rise to concentrations as high as 20-40 nM (Augustsson et al., *J Thromb Haemost.* 2013, 11:s2, PA 4.14-2) when certain known TFPI antibodies, such as the mAb 0001 antibody disclosed in Augustsson et al. supra, forms a complex with TFPI in the circulation. In vivo administration of TFPI antibodies may, therefore, cause TFPI/antibody complexes to accumulate to concentrations that are much higher than the pre-dose plasma concentration of TFPI. Accumulation may, in cases where the inhibitory activity of TFPI/antibody complexes is not fully neutralised, reverse the effect of an otherwise procoagulant TFPI antibody resulting in a net anticoagulant effect.

The inventors envisage that the antibodies disclosed herein, and pharmaceutical compositions comprising them, may address such limitations.

SUMMARY

The present invention relates to an antibody that specifically binds to an epitope in the N-terminal part of tissue factor pathway inhibitor.

In one aspect the invention relates to a TFPI antibody which binds to a TFPI epitope comprising at least one of the following N-terminal amino acid residues Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 of SEQ ID NO: 1.

In one aspect of the invention the TFPI antibody epitope comprises the following N-terminal amino acid residues Arg 41, Arg 65 and Glu 67 of SEQ ID NO: 1.

In one aspect an antibody according to the invention neutralises TFPI inhibition of the TF/FVIIa complex by, for example, competing with TF/FVIIa for binding to TFPI-KPI-1. A TFPI (1-79) binding antibody which binds to, shields or conformationally modifies the TF/FVIIa binding surface, or parts thereof, on TFPI (SEQ ID NO: 1) and thereby functionally blocks the TFPI-TF/FVIIa interaction, may neutralize TFPI inhibition of the TF/FVIIa complex.

In another aspect an antibody according to the invention neutralises the stimulatory effect of TFPI KPI-1 on the reactions leading to the formation of tight complex between TFPI KPI-2 and FXa.

In another aspect a TFPI (1-79) antibody according to the invention binds and neutralises all forms of TFPI.

In one aspect an antibody according to the invention neutralises TFPI, even under circumstances where total TFPI levels in the circulation are elevated, and moreover normalises thrombin generation under these conditions.

The invention also relates to a pharmaceutical formulation comprising at least one antibody capable of specifically binding to an epitope in TFPI (1-79) and at least one pharmaceutically acceptable excipient.

An antibody of the invention, or a pharmaceutical formulation comprising it, may be used as a medicament—such as in the treatment of a subject with a coagulopathy.

BRIEF DESCRIPTION OF THE DRAWINGS

FIG. 1 shows the effect of several TFPI (1-79) antibodies on thrombin generation (TGT assay), as measured using a pool of normal human plasma (NHP) under haemophilia A-like conditions that were obtained by adding 100 μg/ml FVIII antibody.

FIG. 2 shows the effect of several TFPI (1-79) antibodies on thrombin generation (TGT assay), as measured using a pool of NHP under conditions of elevated TFPIα levels obtained by adding 5 nM recombinant full-length TFPIα to the NHP. Haemophilia A-like conditions were obtained by addition of 100 μg/ml FVIII antibody.

BRIEF DESCRIPTION OF THE SEQUENCES

SEQ ID NO: 1 represents the amino acid sequence of human TFPIα.

SEQ ID NO: 2 represents the amino acid sequence of TFPI (1-79).

SEQ ID NO: 3 represents the amino acid sequence of TFPI (1-161).

SEQ ID NO: 4 represents the amino acid sequence of the variable heavy chain of monoclonal antibody (mAb) 2F3.

SEQ ID NO: 5 represents the amino acid sequence of the variable light chain of monoclonal antibody (mAb) 2F3.

SEQ ID NO: 6 represents the amino acid sequence of the variable heavy chain of monoclonal antibody (mAb) 2F22.

SEQ ID NO: 7 represents the amino acid sequence of the variable light chain of monoclonal antibody (mAb) 2F22.

SEQ ID NO: 8 represents the amino acid sequence of the variable heavy chain of monoclonal antibody (mAb) 2F45.

SEQ ID NO: 9 represents the amino acid sequence of the variable light chain of monoclonal antibody (mAb) 2F45.

SEQ ID NO: 10 represents the amino acid sequence of the variable heavy chain of monoclonal antibody (mAb) 1F91

SEQ ID NO: 11 represents the amino acid sequence of the variable light chain of monoclonal antibody (mAb) 1F91.

SEQ ID NO: 12 represents the amino acid sequence of the variable heavy chain of monoclonal antibody (mAb) 2F35.

SEQ ID NO: 13 represents the amino acid sequence of the variable light chain of monoclonal antibody (mAb) 2F35.

SEQ ID NO: 14 represents the nucleic acid sequence of the primer used for cloning antibody heavy chains.

SEQ ID NO: 15 represents the nucleic acid sequence of the primer used for cloning antibody light chains.

SEQ ID NO: 16 represents the amino acid sequence of the truncated murine-human chimeric heavy chain of Fab 0296.

SEQ ID NO: 17 represents the amino acid sequence of the murine-human chimeric light chain of monoclonal antibody mAb 0294 and Fab 0296.

SEQ ID NO: 18 represents the amino acid sequence of tagged TFPI KPI-1/N-terminal.

SEQ ID NO: 19 represents the amino acid sequence of the murine-human chimeric heavy chain of monoclonal antibody mAb 0294.

SEQ ID NO: 20 represents the amino acid sequence the truncated murine-human chimeric heavy chain of Fab 0295.

DESCRIPTION

Mature human TFPIα is a 276 amino acid protein (SEQ ID NO: 1) which consists of an acidic N-terminal region, three tandem Kunitz-type Protease Inhibitor domains (KPI-1, KPI-2 and KPI-3) interspersed by linker regions and a basic C-terminal region. KPI-1, KPI-2 and KPI-3 are defined as residues 26-76, residues 97-147 and residues 189-239, respectively, of SEQ ID NO: 1. Mature TFPIβ is a glycosylphosphatidylinositol (GPI)-anchored 193 amino acid protein of which the first 181 amino acids are identical to TFPIα (corresponding to residues 1-181 of SEQ ID NO: 1) but wherein the C-terminal 12 amino acid sequence is unrelated to TFPIα and has a GPI-linkage added to residue 193.

The present invention relates to an antibody that is capable of binding a region of TFPI, that represents the acidic N-terminal region and KPI-1 domain of TFPI, or any portion thereof.

The term "TFPI", as used herein, encompasses any naturally occurring form of TFPI which may be derived from any suitable organism. For example, TFPI for use as described herein may be mammalian TFPI, such as human, mouse, rabbit, rat, primate, bovine, ovine, or porcine TFPI. Preferably, the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. Variant TFPI molecules may be characterised by having the same type of activity as naturally occurring TFPI, such as the ability to neutralise the catalytic activity of FXa, or the ability to inhibit a complex of TF/FVIIa or the ternary TF/FVIIa/FXa complex.

The term "antibody" herein refers to a protein, derived from a germline immunoglobulin sequence, which is capable of specifically binding to an antigen or a portion thereof: namely TFPI (1-79). The term antibody includes full length antibodies of any class (or isotype), that is, IgA, IgD, IgE, IgG, IgM and/or IgY. An antibody that specifically binds to an antigen, or portion thereof, may bind exclusively to that antigen, or a portion thereof, or it may bind to a limited number of homologous antigens, or portions thereof.

Natural full-length antibodies usually comprise at least four polypeptide chains: two heavy (H) chains and two light (L) chains that are connected by disulfide bonds. In some cases, natural antibodies consist of fewer than four chains, as in the case of the heavy chain only antibodies that are found in camelids ($V_H H$ fragments) and the IgNARs found in Chondrichthyes. One class of immunoglobulins of particular pharmaceutical interest is the class of IgGs. In humans, the IgG class may be divided into four sub-classes: IgG1, IgG2, IgG3 and IgG4, based on the sequence of their heavy chain constant regions. The light chains can be divided into two types: kappa and lambda chains, based on differences in their sequence composition. IgG molecules consist of two heavy chains, interlinked by two or more disulfide bonds, and two light chains, each attached to a heavy chain by a disulfide bond. An IgG heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs) or hypervariable regions (HvRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The variable domains with the hypervariable regions of the heavy and light chains form a domain that is capable of interacting with an antigen, whilst the constant region of an antibody may mediate binding of the immunoglobulin to host tissues or factors, including, but not limited to various cells of the immune system (effector cells), Fc receptors and the first component (C1q) of the C1 complex of the classical complement system.

Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Antibodies of the invention may be monoclonal antibodies, in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in vitro translation. Antibodies or fragments thereof may also be recombinantly expressed as cell surface bound molecules, by means of, e.g., a phage display, bacterial display, yeast display, mammalian cell display, ribosome or mRNA display. Once produced, antibodies may be screened for their ability to bind TFPI, including subdomains such as TFPI (1-79) (SEQ ID NO: 2).

Various antigen-binding fragments of antibodies may also be antibodies according to the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as human TFPI (1-79) or another target molecule, as described herein. Examples of antigen-binding fragments include Fab, Fab', Fab$_2$, Fab'$_2$, FabS, Fv (typically the VL and VH domains of a single arm of an antibody), single-chain Fv (scFv; see e.g. Bird et al., *Science* 1988; 242:423-426; and Huston et al. PNAS 1988; 85:5879-5883), dsFv, Fd (typically the VH and CHI domain) and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., III et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, *Nat Biotechnol* 2005; 23:1126-1136; WO2005040219, and U.S. Patent Applications 20050238646 and 20020161201. These antibody fragments may be obtained using conventional techniques known to those of skill in the art, and the fragments may be screened for utility in the same manner as intact antibodies.

"Fab fragments" of an antibody, including "Fab", "Fab'", and "Fab'$_2$" fragments, are derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and the first constant domain (CH1) of the heavy chain. "Fab'$_2$" fragments comprise a pair of "Fab'" fragments that are generally covalently linked by their hinge cysteines. A Fab' is formally derived from a Fab'$_2$ fragment by cleavage of the hinge disulfide bonds connecting the heavy chains in the Fab'$_2$. Other chemical couplings than disulfide linkages of antibody fragments are also known in the art. A Fab fragment retains the ability of the parent antibody to bind to its antigen, potentially with a lower affinity. Fab'$_2$ fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are generally devoid of effector functions. Fab fragments may be produced by methods known in the art, either by enzymatic cleavage of an antibody, e.g., using papain to obtain the Fab or pepsin to obtain the Fab'$_2$, Fab fragments including Fab, Fab', Fab'$_2$ may also be produced recombinantly using techniques that are well known to the person skilled in the art.

An "Fv" fragment is an antibody fragment that contains a complete antigen recognition and binding site, and generally comprises a dimer of one heavy and one light chain variable domain in an association that can be covalent in nature; for example, in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen binding specificity to the antibody. However, even a single variable domain comprising only three hypervariable regions specific for an antigen can retain the ability to recognise and bind antigen, although usually at a lower affinity than the entire binding site (Cai & Garen, *Proc. Natl.*

*Acad. Sci. USA,* 93: 6280-6285, 1996). For example, naturally occurring camelid antibodies that only have a heavy chain variable domain (VHH) can bind antigen (Desmyter et al., *J. Biol. Chem.,* 277: 23645-23650, 2002; Bond et al., *J. Mol. Biol.* 2003; 332: 643-655).

"Single-chain Fv" or "scFv" antibody fragments comprise the VH and VL domains of an antibody, where these domains are present in a single polypeptide chain. Generally, the Fv polypeptide further comprises a polypeptide linker between the VH and VL domains that enables the scFv to form the desired structure for antigen binding. For a review of scFv, see Pluckthun, 1994, In: *The Pharmacology of Monoclonal Antibodies, Vol.* 113, Rosenburg and Moore eds. Springer-Verlag, New York, pp. 269-315.

The term "diabodies" refers to small antibody fragments with two antigen-binding sites, in which the fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA,* 90:6444-6448.

The expression "linear antibodies" refers to antibodies as described in Zapata et al., 1995, *Protein Eng.,* 8(10):1057-1062. Briefly, these antibodies contain a pair of tandem Fd segments (VH-CH1-VH-CH1) that, together with complementary light chain polypeptides, form a pair of antigen binding regions.

The term "monobody" as used herein, refers to an antigen binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen binding molecules connected by a disulfide bond. The heavy chain variable domain comprises one or more hypervariable regions, preferably a CDRH3 or HVL-H3 region.

The term "antigen" may, herein, refer to the entity used for immunisation of an immunocompetent vertebrate to produce the antibody, or fragment thereof, that recognises it. In the context of the current invention, antigens suitable for immunisation include full length human TFPIα, human TFPI (1-79) and human TFPI (1-161). The term antigen is otherwise intended to include target molecules that are specifically recognised by the antibody, thus including fragments or mimics of the molecule used in the immunisation process, or used for other methods of isolating/generating and characterising antibodies, e.g., phage display, ELISA or SPR.

An antibody according to the current invention may be able to compete with another molecule, such as a naturally occurring ligand or receptor or another antibody, for binding to TFPI and thereby affect functions associated with these interactions. The ability of an antibody to compete with a natural ligand/receptor may be assessed by various activity assays measuring the effect on the apparent $K_I$ for TFPI inhibition. $K_D$ values may then be deduced from apparent $K_I$ values Antibody fragments may thus be obtained using conventional recombinant or protein engineering techniques and the fragments can be screened for binding to TFPI or subdomains thereof, such as human TFPI (1-79) in the same manner as intact antibodies.

Antibody fragments of the invention may be made by truncation, e.g., by removal of one or more amino acids from the N and/or C-terminal ends of a polypeptide. Fragments may also be generated by one or more internal deletions.

Antibodies of the current invention may be human or humanised antibodies. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic non-human animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains sequences (CDR regions or parts thereof) derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for, e.g., affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant regions.

The fragment crystallisable region ("Fc region"/"Fc domain") of an antibody is the C-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprises one or more, and perhaps all of the following mutations that will result in decreased affinity to certain Fc receptors (L234 Å, L235E and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilise inter heavy chain disulphide bridge formation at the hinge (see, e.g., Angal et al., *Mol. Immunol.* 1993; 30:105-8).

Antibodies or fragments thereof may be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain (Kabat et al. (1991) Sequences of Proteins of Immunological Interest, Fifth Edition, U.S. Department of Health and Human Services, NIH Publication No. 91-3242). Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, *J. Mol. Biol.* 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The original CDRs of an antibody can be engineered in order to improve, for example, its affinity, functionality and biophysical properties. Antibody CDRs can be engineered by introduction or addition of germline residues or non-germline residues at any position. Modification of the CDR amino acid composition can result in elimination of predicted immunogenic epitopes, optimisation of biophysical properties, such as viscosity, aggregation, elimination of modification hot-spots such as de-amidation, iso-aspartic acid formation or methionine oxidation sites. Removal of cysteine residues in the CDRs is also desirable as this prevents aberrant disulphide bond formation or shuffling. Optimisation of the biochemical profile of an antibody may also be obtained, e.g., through elimination of potential glycosylation sites. Optimisation of the CDR regions may also result in improved production profile. CDR modifications may also result in optimisation of the antibody-antigen interface, by paratope optimisation or redesign. Such optimisation may include introduction of amino acids where side chain chemistry allows for novel interactions with the antigen. Optimisation can also result in the elimination of sterical obstructions in the paratope-epitope interaction or in optimisation of the CDR loop conformation, flexibility or rigidity.

Said mutations can be introduced in the CDR regions by design, using, e.g., site-directed mutagenesis, or randomly by, e.g., error-prone PCR or synthetically diversified DNA fragments or PCR primers. Modification can also be introduced by shuffling CDR sequences from other antibodies that specifically bind the same antigen.

The term "framework region" or "FR" residues refer to those VH or VL amino acid residues that are not within the CDRs, as defined herein.

An antibody of the invention may comprise a CDR region from one or more of the specific antibodies disclosed herein, such as a CDR region from within SEQ ID NOs: 4 to 13, as defined using Kabat or Chothia numbering or according to the sequential amino acid numbering disclosed herein.

An antibody according to the invention may have a heavy chain comprising:
- a CDR1 sequence corresponding to amino acids 31 to 35 of SEQ ID NO: 4 (SYGVH), wherein one of these amino acid residues may be substituted by a different amino acid residue; and/or
- a CDR2 sequence corresponding to amino acids 50 to 65 of SEQ ID NO: 4 (VIWRGGSTDFNAAFMS), wherein one, two or three of these amino acids may be substituted by a different amino acid residue; and/or
- a CDR3 sequence corresponding to amino acids 98 to 110 of SEQ ID NO: 4 (NSHGNYVGYAMDY), wherein one or two of these amino acid residues may be substituted by a different amino acid.

An antibody according to the invention may have a light chain comprising:
- a CDR1 sequence corresponding to amino acids 24 to 34 (KASENVGAAVA) of SEQ ID NO: 5, wherein one, two or three of these amino acid residues may be substituted by a different amino acid residue; and/or
- a CDR2 sequence corresponding to amino acids 50 to 56 (SASNRYT) of SEQ ID NO: 5, wherein one of these amino acid residues may be substituted by a different amino acid residue; and/or
- a CDR3 sequence corresponding to amino acids 89 to 96 (QQYTNYPT) of SEQ ID NO: 5, wherein one of these amino acid residues may be substituted by a different amino acid residue.

An antibody according to the invention may have a heavy chain comprising:
- a CDR1 sequence corresponding to amino acids 31 to 35 of SEQ ID NO: 6 (NYGVH), wherein one of these amino acid residues may be substituted by a different amino acid residue; and/or
- a CDR2 sequence corresponding to amino acids 50 to 65 of SEQ ID NO: 6 (VIWRGGSIDYNAAFMS), wherein one, two or three of these amino acids may be substituted by a different amino acid residue; and/or
- a CDR3 sequence corresponding to amino acids 98 to 110 of SEQ ID NO: 6 (NSHGNYVGYAMDY), wherein one or two of these amino acid residues may be substituted by a different amino acid.

An antibody according to the invention may have a light chain comprising:
- a CDR1 sequence corresponding to amino acids 24 to 34 (KASQSVGPAVA) of SEQ ID NO: 7, wherein one, two or three of these amino acid residues may be substituted by a different amino acid residue; and/or
- a CDR2 sequence corresponding to amino acids 50 to 56 (SASNRYT) of SEQ ID NO: 7, wherein one of these amino acid residues may be substituted by a different amino acid residue; and/or
- a CDR3 sequence corresponding to amino acids 89 to 96 (QQYTSYPT) of SEQ ID NO: 7, wherein one of these amino acid residues may be substituted by a different amino acid residue.

An antibody according to the invention may have a heavy chain comprising:
- a CDR1 sequence corresponding to amino acids 31 to 35 of SEQ ID NO: 8 (GYGVH), wherein one of these amino acid residues may be substituted by a different amino acid residue; and/or
- a CDR2 sequence corresponding to amino acids 50 to 65 of SEQ ID NO: 8 (VIWRGGSIDYNAAFMS), wherein one, two or three of these amino acids may be substituted by a different amino acid residue; and/or
- a CDR3 sequence corresponding to amino acids 98 to 110 of SEQ ID NO: 8 (NSHGNYVGYAMDY), wherein one or two of these amino acid residues may be substituted by a different amino acid.

An antibody according to the invention may have a light chain comprising:
- a CDR1 sequence corresponding to amino acids 24 to 34 (KASQNVGTAVA) of SEQ ID NO: 9, wherein one, two or three of these amino acid residues may be substituted by a different amino acid residue; and/or
- a CDR2 sequence corresponding to amino acids 50 to 56 (SASNRYT) of SEQ ID NO: 9, wherein one of these amino acid residues may be substituted by a different amino acid residue; and/or
- a CDR3 sequence corresponding to amino acids 89 to 96 (QQYTSYPT) of SEQ ID NO: 9, wherein one of these amino acid residues may be substituted by a different amino acid residue.

An antibody according to the invention may have a heavy chain comprising:
- a CDR1 sequence corresponding to amino acids 31 to 36 of SEQ ID NO: 10 (SDYAWN), wherein one of these amino acid residues may be substituted by a different amino acid residue; and/or
- a CDR2 sequence corresponding to amino acids 51 to 66 of SEQ ID NO: 10 (YISYSGSTSYNPSLKS), wherein one, two or three of these amino acids may be substituted by a different amino acid residue; and/or
- a CDR3 sequence corresponding to amino acids 99 to 104 of SEQ ID NO: 10 (WAYDGP), wherein one of these amino acid residues may be substituted by a different amino acid.

An antibody according to the invention may have a light chain comprising:
- a CDR1 sequence corresponding to amino acids 24 to 33 (RASSSVSHMH) of SEQ ID NO: 11, wherein one or two of these amino acid residues may be substituted by a different amino acid residue; and/or
- a CDR2 sequence corresponding to amino acids 49 to 55 (ATSNLAS) of SEQ ID NO: 11, wherein one of these amino acid residues may be substituted by a different amino acid residue; and/or
- a CDR3 sequence corresponding to amino acids 88 to 96 (QQWSSNPFT) of SEQ ID NO: 11, wherein one of these amino acid residues may be substituted by a different amino acid residue.

An antibody according to the invention may have a heavy chain comprising:

a CDR1 sequence corresponding to amino acids 31 to 35 of SEQ ID NO: 12 (DYYIH), wherein one of these amino acid residues may be substituted by a different amino acid residue; and/or a CDR2 sequence corresponding to amino acids 50 to 66 of SEQ ID NO: 12 (WIDPENGNTIFDPKFQG), wherein one, two or three of these amino acids may be substituted by a different amino acid residue; and/or a CDR3 sequence corresponding to amino acids 99 to 105 of SEQ ID NO: 12 (RWYAMDY), wherein one of these amino acid residues may be substituted by a different amino acid.

An antibody according to the invention may have a light chain comprising:

a CDR1 sequence corresponding to amino acids 24 to 39 (KSSQSLLYTNGKTYLN) of SEQ ID NO: 13, wherein one, two or three of these amino acid residues may be substituted by a different amino acid residue; and/or a CDR2 sequence corresponding to amino acids 55 to 61 (LVSKLDS) of SEQ ID NO: 13, wherein one of these amino acid residues may be substituted by a different amino acid residue; and/or a CDR3 sequence corresponding to amino acids 94 to 102 (LQSTHFPWT) of SEQ ID NO: 13, wherein one of these amino acid residues may be substituted by a different amino acid residue.

The term "epitope", as used herein, is defined in the context of a molecular interaction between an "antigen binding polypeptide", such as an antibody and its corresponding antigen. Generally, "epitope" refers to the area or region on an antigen to which an antibody specifically binds, i.e. the area or region in physical contact with the antibody. Physical contact may be defined using various criteria (e.g., a distance cut-off of 2-6 Å, such as 3 Å, such as 4 Å, such as 5 Å; or solvent accessibility) for atoms in the antibody and antigen molecules. A protein epitope may comprise amino acid residues in the antigen that are directly involved in binding to the antibody (also called the immunodominant component of the epitope) and other amino acid residues, which are not directly involved in binding, such as amino acid residues of the antigen which are effectively blocked by the antibody, i.e. amino acid residues within the "solvent-excluded surface" and/or the "footprint" of the antibody.

The term "epitope" herein comprises both types of binding region in any particular region of TFPI that specifically binds to a TFPI antibody, or another TFPI-specific agent according to the invention, unless otherwise stated. TFPI may comprise a number of different epitopes, which may include, without limitation, (1) linear peptide epitopes (2) conformational epitopes which consist of one or more non-contiguous amino acids located near each other in the mature TFPI conformation; and (3) post-translational epitopes which consist, either in whole or part, of molecular structures covalently attached to TFPI, such as carbohydrate groups.

The epitope for a given antibody/antigen pair can be described and characterised at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given antibody/antigen pair may be described differently.

At its most detailed level, the epitope for the interaction between the antigen and the antibody can be described by the spatial coordinates defining the atomic contacts present in the antigen-antibody interaction, as well as information about their relative contributions to the binding thermodynamics. At a less detailed level, the epitope can be characterised by the spatial coordinates defining the atomic contacts between the antigen and antibody. At an even less detailed level the epitope can be characterised by the amino acid residues that it comprises as defined by a specific criteria such as the distance between or solvent accessibility of atoms in the antibody:antigen complex. At a further less detailed level the epitope can be characterised through function, e.g., by competition binding with other antibodies. The epitope can also be defined more generically as comprising amino acid residues for which substitution by another amino acid will alter the characteristics of the interaction between the antibody and antigen.

In the context of an X-ray derived crystal structure defined by spatial coordinates of a complex between an antibody, e.g. a Fab fragment, and its antigen, the term epitope is herein, unless otherwise specified or contradicted by context, specifically defined as being TFPI residues having a heavy atom (i.e. a non-hydrogen atom) within a distance of 4 Å from a heavy atom in the antibody.

From the fact that descriptions and definitions of epitopes, dependant on the epitope mapping method used, are obtained at different levels of detail, it follows that comparison of epitopes for different antibodies on the same antigen can similarly be conducted at different levels of detail.

Epitopes described at the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the antibody to which an antigen specifically binds, i.e., with which it makes physical contact to the antigen.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), Biolayer Interferometry, ELISA or flow cytometry.

An antibody's "bin" can be defined using a single reference antibody or, alternatively, a group of reference antibodies. The resolution on the "bin" identification for a given antibody will increase with the number of reference antibodies used. When using a single reference antibody, if a second antibody is unable to bind to an antigen at the same time as the reference antibody, the second antibody is said to belong to the same "bin" as the reference antibody. In this case, the reference and the second antibody competitively bind to the same part of the antigen and are coined "competing antibodies". If a second antibody is capable of binding to an antigen at the same time as the reference antibody, the second antibody is said to belong to a separate "bin". In this case, the reference and the second antibody do not competitively bind to the same part of the antigen and are coined "non-competing antibodies". When using a group of reference antibodies for "bin" identification, said group of reference antibodies can comprise a group of known or novel antibodies which can be used to define individual antibody "bins" by cross competition analyses, where each antibody within the group is assayed for competition for antigen binding with each member of the group. Antibody A is said to belong to the same "bin" as antibody B when they exhibit the same pattern of binding in the cross-competition analyses. Antibody A is said to belong to a different "bin" than antibody B, when they exhibit a different competition binding profile against one or more of the individual antibodies in the reference group. The competition binding profile is the compiled set of data where each antibody within the group is assayed for the ability to bind antigen at the same time as another member of the group. E.g. the antigen binding profile for antibody A relative to a reference group of antibody 1, 2 and 3 is as follows: A+1=no binding by A; A+2=binding by A; A+3=binding by A. Antibody B has a different competition binding profile compared to antibody A and the two antibodies are said to belong to different "bins" if: B+1=binding by B; B+2=binding by B; B+3=binding by B. Antibody C has a similar binding profile compared to antibody A and the two antibodies are said to belong to the same "bin" if: C+1=no binding by C; C+2=binding by C; C+3=binding by C. As stated the resolution on the "bin" identification for a given antibody will increase with the number of reference antibodies used. Competitive binding assays do not provide information on binding affinities and the assay must be designed in such a way that the tested antibodies are individually capable of binding the antigen sufficiently enough to function as binding competitors.

Assaying antibody binding to variants of an antigen such as those carrying mutations, truncations, deletions, insertions as well as antigen homologs (e.g. species homologs) may also be used for antibody "binning" or to increase the resolution of antibody "binning".

Antibody "binning" does not provide direct information about the epitope. Competing antibodies, i.e., antibodies belonging to the same "bin", may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "binding affinity" is herein used as a measure of the strength of a non-covalent interaction between two molecules, e.g., an antibody, or fragment thereof, and an antigen. The term "binding affinity" is used to describe monovalent interactions (intrinsic activity).

Binding affinity between two molecules, e.g., an antibody, or fragment thereof, and an antigen, through a monovalent interaction may be quantified by determining the equilibrium dissociation constant ($K_D$). In turn, $K_D$ can be determined by measurement of the kinetics of complex formation and dissociation, e.g., by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

An antibody according to the current invention may be able to compete with another molecule, such as a naturally occurring ligand or receptor or another antibody, for binding to TFPI. Therefore, an antibody according to the current invention may be able to bind TFPI with a greater affinity than that of another molecule also capable of binding TFPI. The ability of an antibody to compete with a natural ligand/receptor for binding to an antigen may be assessed by determining and comparing the $K_D$ value for the interactions of interest, such as a specific interaction between an antibody and an antigen, with that of the $K_D$ value of an interaction not of interest. Typically, the $K_D$ for the antibody with respect to the target will be 2-fold, preferably 5-fold, more preferably 10-fold less than the $K_D$ with respect to the other, non-target molecule, such as unrelated material or accompanying material in the environment. More preferably, the $K_D$ will be 50-fold less, such as 100-fold less, or 200-fold less; even more preferably 500-fold less, such as 1,000-fold less or 10,000-fold less. The value of this dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

An antibody of the invention may have a $K_D$ for its target of $1 \times 10^{-7}$M or less, $1 \times 10^{-8}$M or less, or $1 \times 10^{-9}$M or less, or $1 \times 10^{-19}$M or less, $1 \times 10^{-11}$M or less, or $1 \times 10^{-12}$M or less. The $K_D$ of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as between 0.015 nM and 0 nM.

In another aspect, the present invention provides compositions and formulations comprising molecules of the invention, such as the antibodies described herein. For example, the invention provides a pharmaceutical composition that comprises one or more TFPI antibodies of the invention, formulated together with at least one pharmaceutically acceptable excipient.

Accordingly, one object of the invention is to provide a pharmaceutical formulation comprising such a TFPI antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabiliser or a surfactant, as well as various combinations thereof. The use of preservatives, isotonic agents, chelating agents, stabilisers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

An antibody according to the present invention, or a formulation comprising it, may be used to treat a subject with a coagulopathy.

The term "subject", as used herein, includes any human patient, or non-human vertebrate.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopaenias such as Glanzmann's thombasthenia and Bernard-Soulier syndrome. Said haemophilia A or B may be severe, moderate or mild. The clinical severity of haemophilia is determined by the concentration of functional units of FIX/FVIII in the blood and is classified as mild, moderate, or severe. Severe haemophilia is defined by a clotting factor level of <0.01 U/ml corresponding to <1% of the normal level, while moderate and mild patients have levels from 1-5% and >5%, respectively. Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case, otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

A non-limiting example of an iatrogenic coagulopathy is an overdose of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

Following is a non-limiting list of embodiments of the invention:

EMBODIMENTS

1. An antibody, or fragment thereof, that is capable of specifically binding to an epitope present in amino acid residues 1 to 79 of human TFPI (SEQ ID NO: 1).
2. The antibody or fragment thereof according to embodiment 1, which is capable of binding an epitope present in amino acid residues 26 to 76 (KPI-1) of human TFPI.
3. The antibody or fragment thereof according to any one of embodiments 1 to 2, which has a $K_d$ equal to or less than 1E-08 M, as determined using surface plasmon resonance.
4. The antibody or fragment thereof according to any one of embodiments 1 to 3, the heavy chain of which comprises:
    a CDR1 sequence corresponding to amino acids 31 to 35 of SEQ ID NO: 4 (SYGVH), wherein one of these amino acid residues may be substituted by a different amino acid residue; and/or
    a CDR2 sequence corresponding to amino acids 50 to 65 of SEQ ID NO: 4 (VIWRGGSTDFNAAFMS), wherein one, two or three of these amino acids may be substituted by a different amino acid residue; and/or
    a CDR3 sequence corresponding to amino acids 98 to 110 of SEQ ID NO: 4 (NSHGNYVGYAMDY), wherein one or two of these amino acid residues may be substituted by a different amino acid.
5. The antibody or fragment thereof according to any one of embodiments 1 to 3, the heavy chain of which comprises:
    a CDR1 sequence corresponding to amino acids 31 to 35 of SEQ ID NO: 6 (NYGVH), wherein one of these amino acid residues may be substituted by a different amino acid residue; and/or a CDR2 sequence corresponding to amino acids 50 to 65 of SEQ ID NO: 6 (VIWRGGSIDYNAAFMS), wherein one, two or three of these amino acids may be substituted by a different amino acid residue; and/or a CDR3 sequence corresponding to amino acids 98 to 110 of SEQ ID NO: 6 (NSHGNYVGYAMDY), wherein one or two of these amino acid residues may be substituted by a different amino acid.

6. The antibody or fragment thereof according to any one of embodiments 1 to 3, the heavy chain of which comprises:
   a CDR1 sequence corresponding to amino acids 31 to 35 of SEQ ID NO: 8 (GYGVH), wherein one of these amino acid residues may be substituted by a different amino acid residue; and/or
   a CDR2 sequence corresponding to amino acids 50 to 65 of SEQ ID NO: 8 (VIWRGGSIDYNAAFMS), wherein one, two or three of these amino acids may be substituted by a different amino acid residue; and/or
   a CDR3 sequence corresponding to amino acids 98 to 110 of SEQ ID NO: 8 (NSHGNYVGYAMDY), wherein one or two of these amino acid residues may be substituted by a different amino acid.

7. The antibody or fragment thereof according to any one of embodiments 4 to 6, the light chain of which comprises:
   a CDR1 sequence corresponding to amino acids 24 to 34 (KASENVGAAVA) of SEQ ID NO: 5, wherein one, two or three of these amino acid residues may be substituted by a different amino acid residue; and/or
   a CDR2 sequence corresponding to amino acids 50 to 56 (SASNRYT) of SEQ ID NO: 5, wherein one of these amino acid residues may be substituted by a different amino acid residue; and/or
   a CDR3 sequence corresponding to amino acids 89 to 96 (QQYTNYPT) of SEQ ID NO: 5, wherein one of these amino acid residues may be substituted by a different amino acid residue.

8. The antibody or fragment thereof according to any one of embodiments 4 to 6, the light chain of which comprises:
   a CDR1 sequence corresponding to amino acids 24 to 34 (KASQSVGPAVA) of SEQ ID NO: 7, wherein one, two or three of these amino acid residues may be substituted by a different amino acid residue; and/or
   a CDR2 sequence corresponding to amino acids 50 to 56 (SASNRYT) of SEQ ID NO: 7, wherein one of these amino acid residues may be substituted by a different amino acid residue; and/or
   a CDR3 sequence corresponding to amino acids 89 to 96 (QQYTSYPT) of SEQ ID NO: 7, wherein one of these amino acid residues may be substituted by a different amino acid residue.

9. The antibody or fragment thereof according to any one of embodiments 4 to 6, the light chain of which comprises:
   a CDR1 sequence corresponding to amino acids 24 to 34 (KASQNVGTAVA) of SEQ ID NO: 9, wherein one, two or three of these amino acid residues may be substituted by a different amino acid residue; and/or
   a CDR2 sequence corresponding to amino acids 50 to 56 (SASNRYT) of SEQ ID NO: 9, wherein one of these amino acid residues may be substituted by a different amino acid residue; and/or
   a CDR3 sequence corresponding to amino acids 89 to 96 (QQYTSYPT) of SEQ ID NO: 9, wherein one of these amino acid residues may be substituted by a different amino acid residue.

10. The antibody or fragment thereof according to any one of embodiments 1 to 3, the heavy chain of which comprises:
    a CDR1 sequence corresponding to amino acids 31 to 36 of SEQ ID NO: 10 (SDYAWN), wherein one of these amino acid residues may be substituted by a different amino acid residue; and/or
    a CDR2 sequence corresponding to amino acids 51 to 66 of SEQ ID NO: 10 (YISYSGSTSYNPSLKS), wherein one, two or three of these amino acids may be substituted by a different amino acid residue; and/or
    a CDR3 sequence corresponding to amino acids 99 to 104 of SEQ ID NO: 10 (WAYDGP), wherein one of these amino acid residues may be substituted by a different amino acid.

11. The antibody or fragment thereof according to embodiment 10, the light chain of which comprises:
    a CDR1 sequence corresponding to amino acids 24 to 33 (RASSSVSHMH) of SEQ ID NO: 11, wherein one or two of these amino acid residues may be substituted by a different amino acid residue; and/or
    a CDR2 sequence corresponding to amino acids 49 to 55 (ATSNLAS) of SEQ ID NO: 11, wherein one of these amino acid residues may be substituted by a different amino acid residue; and/or
    a CDR3 sequence corresponding to amino acids 88 to 96 (QQWSSNPFT) of SEQ ID NO: 11, wherein one of these amino acid residues may be substituted by a different amino acid residue.

12. The antibody or fragment thereof according to any one of embodiments 1 to 3, the heavy chain of which comprises:
    a CDR1 sequence corresponding to amino acids 31 to 35 of SEQ ID NO: 12 (DYYIH), wherein one of these amino acid residues may be substituted by a different amino acid residue; and/or
    a CDR2 sequence corresponding to amino acids 50 to 66 of SEQ ID NO: 12 (WIDPENGNTIFDPKFQG), wherein one, two or three of these amino acids may be substituted by a different amino acid residue; and/or
    a CDR3 sequence corresponding to amino acids 99 to 105 of SEQ ID NO: 12 (RWYAMDY), wherein one of these amino acid residues may be substituted by a different amino acid.

13. The antibody or fragment thereof according to embodiment 12, the light chain of which comprises:
    a CDR1 sequence corresponding to amino acids 24 to 39 (KSSQSLLYTNGKTYLN) of SEQ ID NO: 13, wherein one, two or three of these amino acid residues may be substituted by a different amino acid residue; and/or
    a CDR2 sequence corresponding to amino acids 55 to 61 (LVSKLDS) of SEQ ID NO: 13, wherein one of these amino acid residues may be substituted by a different amino acid residue; and/or
    a CDR3 sequence corresponding to amino acids 94 to 102 (LQSTHFPWT) of SEQ ID NO: 13, wherein one of these amino acid residues may be substituted by a different amino acid residue.

14. The antibody or fragment thereof according to any one of embodiments 1 to 3, the heavy chain of which comprises:
    a CDR1 sequence corresponding to amino acids 31 to 35 of SEQ ID NO: 4 (SYGVH), SEQ ID NO: 6 (NYGVH) or SEQ ID NO: 8 (GYGVH); and
    a CDR2 sequence corresponding to amino acids 50 to 65 of SEQ ID NO: 4 (VIWRGGSTDFNAAFMS), SEQ ID NO: 6 (VIWRGGSIDYNAAFMS) or SEQ ID NO: 8 (VIWRGGSIDYNAAFMS); and a CDR3 sequence corresponding to amino acids 98 to 110 of SEQ ID NO: 4, SEQ ID NO: 6 or SEQ ID NO: 8 (NSHGNYVGYAMDY);

and the light chain of which comprises:

a CDR1 sequence corresponding to amino acids 24 to 34 of SEQ ID NO: 5 (KASENVGAAVA), SEQ ID NO: 7 (KASQSVGPAVA) or SEQ ID NO: 9 (KASQNVGTAVA); and a CDR2 sequence corresponding to amino acids 50 to 56 of SEQ ID NO: 5, SEQ ID NO: 7 or SEQ ID NO: 9 (SASNRYT); and a CDR3 sequence corresponding to amino acids 89 to 96 of SEQ ID NO: 5 (QQYTNYPT), SEQ ID NO: 7 (QQYTSYPT) or SEQ ID NO: 9 (QQYTSYPT).

15. The antibody or fragment thereof according to embodiment 10, the heavy chain of which comprises:

a CDR1 sequence corresponding to amino acids 31 to 36 of SEQ ID NO: 10 (SDYAWN); and a CDR2 sequence corresponding to amino acids 51 to 66 of SEQ ID NO: 10 (YISYSGSTSYNPSLKS); and a CDR3 sequence corresponding to amino acids 99 to 104 of SEQ ID NO: 10 (WAYDGP);

and the light chain of which comprises:

a CDR1 sequence corresponding to amino acids 24 to 33 (RASSSVSHMH) of SEQ ID NO: 11; and a CDR2 sequence corresponding to amino acids 49 to 55 (ATSNLAS) of SEQ ID NO: 11; and a CDR3 sequence corresponding to amino acids 88 to 96 (QQWSSNPFT) of SEQ ID NO: 11.

16. The antibody or fragment thereof according to embodiment 12, the heavy chain of which comprises:

a CDR1 sequence corresponding to amino acids 31 to 35 of SEQ ID NO: 12 (DYYIH); and a CDR2 sequence corresponding to amino acids 50 to 66 of SEQ ID NO: 12 (WIDPENGNTIFDPKFQG); and a CDR3 sequence corresponding to amino acids 99 to 105 of SEQ ID NO: 12 (RWYAMDY);

and the light chain of which comprises:

a CDR1 sequence corresponding to amino acids 24 to 39 (KSSQSLLYTNGKTYLN) of SEQ ID NO: 13; and a CDR2 sequence corresponding to amino acids 55 to 61 (LVSKLDS) of SEQ ID NO: 13; and a CDR3 sequence corresponding to amino acids 94 to 102 (LQSTHFPWT) of SEQ ID NO: 13.

17. An antibody or fragment thereof which competes with the antibody according to any one of the preceding embodiments for binding to TFPI (1-79), as determined using Biolayer Interferometry.

18. An antibody or fragment thereof which belongs to the same bin as an antibody according to any one of the preceding embodiments, as determined using Biolayer Interferometry.

19. The antibody or fragment thereof according to any one of the preceding embodiments, which is a monoclonal antibody.

20. The antibody or fragment thereof according to any one of the preceding embodiments, which is a humanised antibody.

21. The antibody fragment according to any one of the preceding embodiments, which is selected from the group consisting of a Fab, a Fab', a $Fab_2$, a $Fab'_2$ and a scFv fragment.

22. A pharmaceutical formulation comprising the antibody, or fragment thereof, according to any one of embodiments 1 to 21 and at least one pharmaceutically acceptable excipient.

23. The antibody or fragment thereof according to any one of embodiments 1 to 21, or the pharmaceutical formulation according to embodiment 22, for use as a medicament.

24. The antibody or fragment thereof according to any one of embodiments 1 to 21, or the pharmaceutical formulation according to embodiment 22, for use in the treatment of a subject with a coagulopathy.

25. The antibody or fragment thereof for use according to embodiment 24, wherein said subject has any congenital, acquired and/or iatrogenic coagulopathy, such as haemophilia A, with or without inhibitors, and haemophilia B, with or without inhibitors.

26. A method of treating a subject with a coagulopathy, comprising administering to said subject the antibody or fragment thereof according to any one of embodiments 1 to 21.

The invention is, furthermore, exemplified by the following aspects:

1. An isolated antibody or fragment thereof that specifically binds to an epitope present in amino acid residues 1 to 79 of human TFPI (SEQ ID NO: 1).
2. The antibody or fragment thereof according to aspect 1, which specifically binds an epitope present in amino acid residues 26 to 76 (KPI-1) of human TFPI (SEQ ID NO:1).
3. The antibody or fragment thereof according to aspect 1, which specifically binds an epitope present in human TFPI wherein said epitope comprises at least one of the following amino acid residues L16, P17, L19, K20, L21, M22, F25, C35, A37, M39, R41, Y56, G57, G58, C59, E60, G61, N62, Q63, R65, F66, E67, E71 and M75 of SEQ ID NO: 1.
4. The antibody or fragment thereof according to aspect 3, which specifically binds an epitope present in human TFPI wherein said epitope comprises at least one of the following amino acid residues R41, R65 and E67 of SEQ ID NO: 1.
5. The antibody or fragment thereof according to aspect 1, which has a $K_d$ equal to or less than 1E-08 M, as determined using surface plasmon resonance.
6. An isolated antibody which specifically binds human TFPI wherein the heavy chain of said antibody comprises amino acid residues V in a position corresponding to position 2,
F in a position corresponding to position 27,
Y in a position corresponding to position 32,
W in a position corresponding to position 52,
R in a position corresponding to position 53,
G in a position corresponding to position 54,
G in a position corresponding to position 55,
S in a position corresponding to position 56,
I in a position corresponding to position 57,
D in a position corresponding to position 58,
Y in a position corresponding to position 59,
A in a position corresponding to position 61,
M in a position corresponding to position 64,
K in a position corresponding to position 97,
S in a position corresponding to position 99,
H in a position corresponding to position 100,
N in a position corresponding to position 102,
Y in a position corresponding to position 103,
V in a position corresponding to position 104,
G in a position corresponding to position 105, and
Y in a position corresponding to position 106
of SEQ ID NO: 16, and
wherein the light chain of said antibody comprises amino acid residues
P in a position corresponding to position 31,
A in a position corresponding to position 32, Y in a position corresponding to position 49,
S in a position corresponding to position 50,
N in a position corresponding to position 53,
Y in a position corresponding to position 55,
T in a position corresponding to position 56,
Y in a position corresponding to position 91,
T in a position corresponding to position 92,
S in a position corresponding to position 93, and
Y in a position corresponding to position 94
of SEQ ID NO: 17.

7. The antibody according to aspect 1, the heavy chain of which comprises:
   a CDR1 sequence corresponding to amino acids 31 to 35 of SEQ ID NO: 4 (SYGVH), SEQ ID NO: 6 (NYGVH) or SEQ ID NO: 8 (GYGVH), wherein one of these amino acid residues may be substituted by a different amino acid residue; and/or
   a CDR2 sequence corresponding to amino acids 50 to 65 of SEQ ID NO: 4 (VIWRGGSTDFNAAFMS), SEQ ID NO: 6 (VIWRGGSIDYNAAFMS) or SEQ ID NO: 8 (VIWRGGSIDYNAAFMS), wherein one, two or three of these amino acids may be substituted by a different amino acid residue; and/or
   a CDR3 sequence corresponding to amino acids 98 to 110 of SEQ ID NO: 4 (NSHGNYVGYAMDY), SEQ ID NO: 6 or SEQ ID NO: 8 (NSHGNYVGYAMDY), wherein one or two of these amino acid residues may be substituted by a different amino acid.

8. The antibody or fragment thereof according to aspect 1 or 7, the light chain of which comprises:
   a CDR1 sequence corresponding to amino acids 24 to 34 (KASENVGAAVA) of SEQ ID NO: 5, SEQ ID NO: 7 (KASQSVGPAVA) or SEQ ID NO: 9 (KASQNVGTAVA), wherein one, two or three of these amino acid residues may be substituted by a different amino acid residue; and/or
   a CDR2 sequence corresponding to amino acids 50 to 56 (SASNRYT) of SEQ ID NO: 5, SEQ ID NO: 7 or SEQ ID NO: 9 (SASNRYT), wherein one of these amino acid residues may be substituted by a different amino acid residue; and/or
   a CDR3 sequence corresponding to amino acids 89 to 96 (QQYTNYPT) of SEQ ID NO: 5, SEQ ID NO: 7 (QQYTSYPT) or SEQ ID NO: 9 (QQYTSYPT), wherein one of these amino acid residues may be substituted by a different amino acid residue.

9. The antibody or fragment thereof according to aspect 1, the heavy chain of which comprises:
   a CDR1 sequence corresponding to amino acids 31 to 35 of SEQ ID NO: 4 (SYGVH), SEQ ID NO: 6 (NYGVH) or SEQ ID NO: 8 (GYGVH); and
   a CDR2 sequence corresponding to amino acids 50 to 65 of SEQ ID NO: 4 (VIWRGGSTDFNAAFMS), SEQ ID NO: 6 (VIWRGGSIDYNAAFMS) or SEQ ID NO: 8 (VIWRGGSIDYNAAFMS); and
   a CDR3 sequence corresponding to amino acids 98 to 110 of SEQ ID NO: 4, SEQ ID NO: 6 or SEQ ID NO: 8 (NSHGNYVGYAMDY);
   and the light chain of which comprises:
   a CDR1 sequence corresponding to amino acids 24 to 34 of SEQ ID NO: 5 (KASENVGAAVA), SEQ ID NO: 7 (KASQSVGPAVA) or SEQ ID NO: 9 (KASQNVGTAVA); and
   a CDR2 sequence corresponding to amino acids 50 to 56 of SEQ ID NO: 5, SEQ ID NO: 7 or SEQ ID NO: 9 (SASNRYT); and
   a CDR3 sequence corresponding to amino acids 89 to 96 of SEQ ID NO: 5 (QQYTNYPT), SEQ ID NO: 7 (QQYTSYPT) or SEQ ID NO: 9 (QQYTSYPT).

10. The antibody or fragment thereof according to aspect 1, the heavy chain of which comprises:
    a CDR1 sequence corresponding to amino acids 31 to 35 of SEQ ID NO: 6 (NYGVH); and
    a CDR2 sequence corresponding to amino acids 50 to 65 of SEQ ID NO: 6 (VIWRGGSIDYNAAFMS); and
    a CDR3 sequence corresponding to amino acids 98 to 110 of SEQ ID NO: 6 (NSHGNYVGYAMDY);
    and the light chain of which comprises:
    a CDR1 sequence corresponding to amino acids 24 to 34 of SEQ ID NO: 7 (KASQSVGPAVA); and
    a CDR2 sequence corresponding to amino acids 50 to 56 of SEQ ID NO: 7 (SASNRYT); and
    a CDR3 sequence corresponding to amino acids 89 to 96 of SEQ ID NO: 7 (QQYTSYPT).

11. The antibody or fragment thereof according to aspect 1, the heavy chain of which comprises:
    a CDR1 sequence corresponding to amino acids 31 to 36 of SEQ ID NO: 10 (SDYAWN), wherein one of these amino acid residues may be substituted by a different amino acid residue; and/or
    a CDR2 sequence corresponding to amino acids 51 to 66 of SEQ ID NO: 10 (YISYSGSTSYNPSLKS), wherein one, two or three of these amino acids may be substituted by a different amino acid residue; and/or
    a CDR3 sequence corresponding to amino acids 99 to 104 of SEQ ID NO: 10 (WAYDGP), wherein one of these amino acid residues may be substituted by a different amino acid,
    and the light chain of which comprises:
    a CDR1 sequence corresponding to amino acids 24 to 33 (RASSSVSHMH) of SEQ ID NO: 11, wherein one or two of these amino acid residues may be substituted by a different amino acid residue; and/or
    a CDR2 sequence corresponding to amino acids 49 to 55 (ATSNLAS) of SEQ ID NO: 11, wherein one of these amino acid residues may be substituted by a different amino acid residue; and/or
    a CDR3 sequence corresponding to amino acids 88 to 96 (QQWSSNPFT) of SEQ ID NO: 11, wherein one of these amino acid residues may be substituted by a different amino acid residue.

12. The antibody or fragment thereof according to aspect 11, the heavy chain of which comprises:
    a CDR1 sequence corresponding to amino acids 31 to 36 of SEQ ID NO: 10 (SDYAWN);
    a CDR2 sequence corresponding to amino acids 51 to 66 of SEQ ID NO: 10 (YISYSGSTSYNPSLKS); and
    a CDR3 sequence corresponding to amino acids 99 to 104 of SEQ ID NO: 10 (WAYDGP);
    and the light chain of which comprises:
    a CDR1 sequence corresponding to amino acids 24 to 33 (RASSSVSHMH) of SEQ ID NO: 11;
    a CDR2 sequence corresponding to amino acids 49 to 55 (ATSNLAS) of SEQ ID NO: 11; and
    a CDR3 sequence corresponding to amino acids 88 to 96 (QQWSSNPFT) of SEQ ID NO: 11.

13. The antibody or fragment thereof according to aspect 1, the heavy chain of which comprises:
    a CDR1 sequence corresponding to amino acids 31 to 35 of SEQ ID NO: 12 (DYYIH), wherein one of these amino acid residues may be substituted by a different amino acid residue; and/or a CDR2 sequence corresponding to amino acids 50 to 66 of SEQ ID NO: 12 (WIDPENGNTIFDPKFQG), wherein one, two or three of these amino acids may be substituted by a different amino acid residue; and/or a CDR3 sequence corresponding to amino acids 99 to 105 of SEQ ID NO: 12 (RWYAMDY), wherein one of these amino acid residues may be substituted by a different amino acid.

and the light chain of which comprises:

a CDR1 sequence corresponding to amino acids 24 to 39 (KSSQSLLYTNGKTYLN) of SEQ ID NO: 13, wherein one, two or three of these amino acid residues may be substituted by a different amino acid residue; and/or a CDR2 sequence corresponding to amino acids 55 to 61 (LVSKLDS) of SEQ ID NO: 13, wherein one of these amino acid residues may be substituted by a different amino acid residue; and/or a CDR3 sequence corresponding to amino acids 94 to 102 (LQSTHFPWT) of SEQ ID NO: 13, wherein one of these amino acid residues may be substituted by a different amino acid residue.

14. The antibody or fragment thereof according to aspect 13, the heavy chain of which comprises:
a CDR1 sequence corresponding to amino acids 31 to 35 of SEQ ID NO: 12 (DYYIH); and
a CDR2 sequence corresponding to amino acids 50 to 66 of SEQ ID NO: 12 (WIDPENGNTIFDPKFQG); and
a CDR3 sequence corresponding to amino acids 99 to 105 of SEQ ID NO: 12 (RWYAMDY);
and the light chain of which comprises:
a CDR1 sequence corresponding to amino acids 24 to 39 (KSSQSLLYTNGKTYLN) of SEQ ID NO: 13; and
a CDR2 sequence corresponding to amino acids 55 to 61 (LVSKLDS) of SEQ ID NO: 13; and
a CDR3 sequence corresponding to amino acids 94 to 102 (LQSTHFPWT) of SEQ ID NO: 13.

15. An isolated antibody or fragment thereof which competes with the antibody according to any one of aspects 3 to 10 for binding to TFPI (1-79), as determined using Biolayer Interferometry.

16. An isolated antibody or fragment thereof which belongs to the same bin as the antibody according to any one of aspects 1 to 14, as determined using Biolayer Interferometry.

17. A pharmaceutical formulation comprising at least one antibody or fragment thereof according to any one of aspects 1 to 16 and at least one pharmaceutically acceptable excipient.

18. The antibody or fragment thereof according to any one of aspects 1 to 16, or the pharmaceutical formulation according to aspect 17, for use as a medicament.

19. The antibody or fragment thereof according to any one of aspects 1 to 16 for use in the treatment of a subject with a coagulopathy.

20. The antibody or fragment thereof for use according to aspect 19, wherein said subject has a congenital, acquired and/or iatrogenic coagulopathy, such as haemophilia A, with or without inhibitors, and haemophilia B, with or without inhibitors.

21. A method of treating a subject with a coagulopathy, comprising administering to said subject the antibody or fragment thereof according to any one of aspects 1 to 16.

The present invention is further illustrated by the following examples which should not be construed as further limiting. The contents of all figures and all references, patents and published patent applications cited throughout this application are expressly incorporated herein by reference.

EXAMPLES

Example 1: Immunisation, Fusion and Screening

RBF mice were immunised with human TFPIα (SEQ ID NO: 1) or TFPI (1-161) (SEQ ID NO: 3). Mice were injected subcutaneously: 20 mg human TFPI was mixed with complete Freund's adjuvant for the first injection. For subsequent immunisations, incomplete Freund's adjuvant was used with the same concentration of the antigen. Ten days after the final immunisation, eye-blood from mice was screened, using ELISA, for human TFPI specific antibodies. Mice with positive serum titres were boosted with 10 μg of human TFPIα or TFPI (1-161) by intravenous injection and sacrificed after three days. The spleens were removed aseptically and dispersed to a single cell suspension. Fusion of spleen cells and myeloma cells was done by means of the PEG-method or by electrofusion. The resulting hybridoma cells were cloned by limiting dilution into microtiter plates. Supernatants from individual hybridomas were initially screened by ELISA for expression of antibodies capable of binding to full-length TFPIα or TFPI (1-161). To identify hybridomas producing antibodies specific for TFPI (1-79), the hybridomas positive for binding to full-length TFPIα or TFPI (1-161) were counter screened for binding to the TFPI-KPI-2 fragment (represented by amino acid residues 97-147 of SEQ ID NO: 1). Hybridomas positive for binding to TFPI (1-161) and negative for binding to the TFPI-KPI-2 fragment were isolated and expanded for production of antibody.

Antibodies were purified from supernatants by standard protein A affinity chromatography and used to determine binding and affinity to human TFPIα and TFPI (1-79) and TFPI neutralising activity in plasma (TGT assay). Hybridomas producing antibodies of interest, i.e., those specific for TFPI (1-79) were subcloned by limited dilution and the original antibody profile was verified for material from subcloned hybridomas. Cells from subcloned hybridomas were used for isolation of RNA and subsequent antibody cloning and sequence identification.

Example 2: Cloning and Sequencing of Mouse Anti-Human TFPI (1-79) Specific mAbs

This example describes cloning and sequencing of the murine heavy chain and light chain sequences of TFPI antibodies mAb 2F3, mAb 2F22, mAb 2F45, mAb 1F56, mAb 1F91 and mAb 2F35. Total RNA was extracted from hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. The reverse primer with the sequence shown in SEQ ID NO: 14 was used for HC (VH domain) amplification and the reverse primer with the sequence shown in SEQ ID NO: 15 was used for LC amplification. PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 *E. coli* (Life Technologies). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at MWG Biotech, Martinsried Germany using M13uni(-21)/M13rev(-29) sequencing primers. Sequences were analysed and annotated using the Vector NTI Advance 11 program (Life Technologies). All kits and reagents were used according to the manufacturer's instructions.

A single unique murine kappa type LC and a single unique murine HC, subclass mIgG1 was identified for each of the hybridomas: mAb 2F3, mAb 2F22, mAb 2F45, mAb 1F91 and mAb 2F35. The LC and HC sequences of mAb 1F56 showed that this antibody is identical in sequence to mAb 1F91. Amino acid sequences for the variable heavy chain and variable light chain sequences (excluding leader peptide sequences) are shown in SEQ ID NOs 4-13. The SEQ ID NOs are listed in Table 1.

Generation of Antibody LC and HC Expression Vectors

CMV promoter-based expression vectors (pTT vectors) were generated for transient expression of mouse-human chimeric versions of mAb 2F22. The pTT vectors are developed for transient protein expression by Yves Durocher (Durocher et al. Nucleic Acid Research, 2002). In addition to the CMV promotor, the pTT-based vectors contain a pMB1 origin, an EBV origin and the Amp resistance gene.

An expression vector was generated for expression of a chimeric mAb 2F22 light chain, carrying the murine 2F22 light chain variable region and a human kappa constant region (SEQ ID NO: 17). Expression vectors were generated for expression of a chimeric mAb 2F22 heavy chain carrying the murine 2F22 heavy chain variable region and a full length human IgG4 (S241P) constant region for mAb 0294 expression (SEQ ID NO: 19) or truncated human IgG4 constant regions for Fab 0296 expression (SEQ ID NO: 16) or Fab 0295 expression (SEQ ID NO: 20). The SEQ ID NOs are listed in Table 1.

pTT-based LC expression vector was generated for transient expression of chimeric mAb 2F22 antibody and antibody fragment. Initially, the region corresponding to the VL domains of mAb 2F22 was PCR amplified in a 2-step reaction from an original TOPO sequencing clone, using primers specific for the N and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame BsiWI restriction site in the VL/CL transition sequence. The amplified fragment was cloned into a linearized pTT-based vector containing the sequence for a human kappa CL domain and subsequently transformed into *E. coli* for selection. The sequence of the final construct was verified by DNA sequencing.

pTT-based HC expression vectors were generated for transient expression of a chimeric mAb 2F22 and Fab 2F22 fragments. The chimeric mAb and Fab fragments are referred to as mAb 0294, Fab 0296 and Fab 0295, respectively. Initially, the region corresponding to the VH domain of mAb 2F22 was PCR amplified in a 2-step reaction from an original TOPO sequencing clone, using primers specific for the N- and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame NheI restriction site at the VH/CH transition. For generation of full length HC expression vector (HC of mAb 0294), the generated VH domain PCR fragment was restriction digested and cloned into a linearized pTT-based vector containing the sequence for a human IgG4 (S241P) constant region. The IgG4 hinge mutation Serine 241 to Proline is included to stabilize the IgG4 antibody by eliminating formation of half-antibodies. The mutated hinge position is referred to as S241P when numbered according to Kabat or alternatively S228P, when numbered according to the EU index.

For generation of the truncated HC expression vector for Fab 0296 expression, the generated VH domain PCR fragment was restriction digested and cloned into a linearized pTT-based vector containing the sequence for a truncated human IgG4 constant region. The IgG4-based HC was truncated in the hinge region after the human IgG4 hinge lysine as seen in the sequence of the Fab 0296 HC (SEQ ID NO: 16). The cloning reaction was subsequently transformed into *E. coli* for selection. The sequence of the final construct was verified by DNA sequencing.

For generation of the truncated HC expression vector for Fab 0295 expression, the generated VH domain PCR fragment was restriction digested and cloned into a linearized pTT-based vector containing the sequence for a second truncated human IgG4 constant region. The IgG4-based HC for Fab 0295 was truncated in the hinge region after the first cysteine of the human IgG4 hinge as seen in the sequence of the Fab 0295 HC (SEQ ID NO: 20). The cloning reaction was subsequently transformed into *E. coli* for selection. The sequence of the final construct was verified by DNA sequencing.

Expression and Purification of mAb and Fab Fragments

The anti-TFPI antibodies and Fab fragments were expressed transiently in suspension cultures of EXPI293F cells (Life Technologies), by co-transfection of the pTT-based LC and HC expression vectors. The following procedure describes the generic transfection protocol used for suspension adapted EXPI293F cells.

EXPI293F Transfection

1) Separate dilutions of DNA and transfection reagent are initially prepared.
   a) Use a total of 1 μg of vector DNA (0.5 ug LC vector and 0.5 ug HC vector) per ml cell culture. Dilute the DNA in Opti-MEM media (Gibco) 50 μl medium/μg DNA, mix and incubate at room temperature (23-25° C.) for 5 min.
   b) Use Expifectamin™ 293 (Life Technologies) as transfection reagent at a concentration of 2.7 μl per μg DNA. Dilute the Expifectamin™ solution 18.5× in Opti-MEM media (Gibco), mix and incubate at room temperature (23-25° C.) for 5 min.
2) Mix DNA and Expifectamin™ 293 dilutions and leave to incubate at room temperature (23-25° C.) for 10 min.

3) Add the DNA-Expifectamin™ 293 mix directly to the EXPI293F cell culture.
   a) At the time of transfection the cell density of the EXPI293F culture should be 2.8-3.2×10⁶ cells/ml.
4) Transfer the transfected cell culture to an orbital shaker incubator at 36.5° C., 8% $CO_2$ and 85-125 rpm.
5) 18 hrs post transfection, add 5 ul Expifectamin™ 293 Transfection Enhancer1/ml culture and 50 ul Expifectamin™ 293 Transfection Enhancer2/ml culture and return culture to an orbital shaker incubator at 36.5° C., 8% $CO_2$ and 85-125 rpm.
6) 5 days post transfection, cell culture supernatants were harvested by centrifugation, followed by filtration through a 0.22 μm PES filter unit (Corning).

General Purification Protocol mAb variants were purified by standard affinity chromatography using MabSelectSuRe resin from GE Healthcare according to manufacturer's instructions. The purified antibodies were buffer exchanged to PBS buffer pH 7.2.

Fab fragments were purified by standard affinity chromatography using KappaSelect resin developed by GE Healthcare. The purified Fab fragments were buffer exchanged to PBS buffer pH 7.2. Quality assessment and concentration determination was done by SEC-HPLC.

TABLE 1

Summary of sequence identified antibody and antibody fragments

| Antibody ID (mAb) domain/chain | SEQ ID NO: |
|---|---|
| 2F3 | |
| VH | 4 |
| VL | 5 |
| 2F22 | |
| VH | 6 |
| VL | 7 |
| HC Fab 0296 | 16 |
| HC Fab 0295 | 20 |
| HC mAb 0294 | 19 |
| LC Fab 0296, Fab 0295 & mAb 0294 | 17 |
| 2F45 | |
| VH | 8 |
| VL | 9 |
| 1F91 | |
| VH | 10 |
| VL | 11 |
| 2F35 | |
| VH | 12 |
| VL | 13 |

VH: heavy chain variable domain,
VL: light chain variable domain,
HC: heavy chain,
LC: light chain.

Example 3: Binding Interaction Analysis

Binding interaction data were obtained by means of Surface Plasmon Resonance in a Biacore T200 instrument. Polyclonal rabbit anti-mouse immunoglobulin (Mouse Antibody Capture Kit, GE Healthcare) was immobilized to a series S CM4 sensor chip (GE Healthcare) in flow-cells 1-4 using the amine coupling protocol available with the Biacore T-200 control software version 2.0 (GE Healthcare) and the reagents provided with the Amine Coupling Kit (GE Healthcare). The relevant mouse monoclonal antibody was captured in flow cell 2, 3, or 4 at a fixed concentration. Different concentrations of human TFPIα or TFPI (1-79) were tested by diluting the sample in running buffer (10 mM HEPES, pH 7.4, 300 mM NaCl, 5 mM $CaCl_2$, 0.05% Surfactant P20, 1 mg/ml BSA). Each sample was assayed using 300 seconds of contact time followed by 420-600 seconds of dissociation time at 30 μl/min flow rate. A buffer blank was also assayed. The sensor surface was regenerated with 10 mM Glycine pH 1.7 either for 180 sec at 30 μl/min flow rate or with two cycles each of 30 seconds at 30 μl/min flow rate.

Monoclonal mouse anti-human IgG (Fc) antibody (Human Antibody Capture Kit, GE Healthcare) was immobilized to a series S CM4 sensor chip (GE Healthcare) in flow-cells 1-2 using the amine coupling protocol available with the Biacore T-200 control software (GE Healthcare) and the reagents provided with the Amine Coupling Kit (GE Healthcare). The relevant antibody Bay 2A8, Bay 2A8-K95L or mAb 0294 (SEQ ID NO: 19 and 17) was captured in flow cell 2 at a fixed concentration. Different concentrations of human TFPIα or TFPI (1-79) were tested as described above. The sensor surface was regenerated with 3M $MgCl_2$ either for 180 sec at 30 μl/min flow rate or with two cycles each of 30 seconds at 30 μl/min flow rate.

Human Fab Binder (Human Fab Capture Kit, GE Healthcare) was immobilized to a series S CM4 sensor chip (GE Healthcare) in flow-cells 1-4 at 9000-10000 response units (RU) using the amine coupling protocol available within the Biacore T-200 control software (GE Healthcare) and the reagents provided with the Amine Coupling Kit (GE Healthcare). The relevant Fab fragments, Fab 0295 (SEQ ID NO: 20 and 17) or Fab 0296 (SEQ ID NO: 16 and 17) were injected at a fixed concentration (0.2 μg/ml) for 180 sec in flow cell 2, 3 or 4 at 10 μl/min flow rate which should give a response of approximately 70-80 RU. Different concentrations of human TFPIα were tested by diluting the sample in running buffer (10 mM HEPES, pH 7.4, 300 mM NaCl, 5 mM $CaCl_2$, 0.05% Surfactant P20, 1 mg/ml BSA). Each sample was assayed using 300 seconds of contact time followed by 600 seconds of dissociation time at 50 μl/min flow rate. A buffer blank was also assayed. The sensor surface was regenerated with 10 mM Glycine pH 2.1 with two cycles each of 30 seconds at 50 μl/min flow rate. The analysis temperature was 25° C. and the sample compartment temperature 10° C.

The Biacore T200 Evaluation software (version 2.0) was used to analyse the data. Determination of binding constants ($k_a$, $k_d$, $K_D$) was obtained assuming a 1:1 interaction of TFPI and the monoclonal antibody of interest.

The data in Table 2 demonstrate that the antibodies of the invention that were tested (mAbs 1F56, 1F91, 2F3, 2F17, 2F22, 2F35, 2F37, 2F39, 2F45, 2F48) bind with high affinity to an epitope within human TFPI (1-79), encompassing the acidic N-terminal peptide and the TFPI-KPI-1 domain.

The data in Table 3 demonstrate that mAb 2F22 expressed as a chimeric antibody mAb 0294: (SEQ ID NO: 17 and 19) and chimeric Fab fragments, Fab 0296 (SEQ ID 17 and 16) and Fab 0295 (SEQ ID 17 and 20) retain high affinity binding to TFPI.

TABLE 2

Binding constants
Binding constants ($k_a$, $k_d$, $K_D$) were obtained assuming a 1:1 interaction of human TFPIα or TFPI (1-79) and the antibody of interest. Bay 2A8 is a human IgG4 (S241P) antibody variant of the 2A8 Fab disclosed in WO2010/017196. Bay 2A8-K95L is a human IgG4 (S241P) antibody variant of Bay 2A8 carrying the K95L substitution (Kabat numbering) in HC CDR3, identical to the substitution found in "Fab B" relative to 2A8 as disclosed in WO2012/135671.

| | Human TFPIα | | | Human TFPI (1-79) | | |
|---|---|---|---|---|---|---|
| Compound | $k_a$ (1/Ms) | $k_d$ (1/s) | $K_D$ (M) | $k_a$ (1/Ms) | $k_d$ (1/s) | $K_D$ (M) |
| 1F56 | 3.68E+05 | 3.61E−03 | 9.81E−09 | 3.75E+05 | 5.05E−03 | 1.35E−08 |
| 1F91 | 3.47E+05 | 3.49E−03 | 1.00E−08 | 3.30E+05 | 5.00E−03 | 1.51E−08 |
| 2F3 | 1.72E+05 | 7.69E−05 | 4.48E−10 | 2.74E+05 | 1.54E−04 | 5.61E−10 |
| 2F17 | 3.03E+05 | 1.39E−03 | 4.57E−09 | 3.61E+05 | 1.69E−03 | 4.68E−09 |
| 2F22 | 2.08E+05 | 1.43E−04 | 6.88E−10 | 2.42E+05 | 2.34E−04 | 9.65E−10 |
| 2F35 | 2.24E+05 | 1.41E−03 | 6.27E−09 | 1.88E+05 | 2.51E−03 | 1.33E−08 |
| 2F37 | 1.92E+05 | 9.50E−04 | 4.94E−09 | 1.69E+05 | 1.84E−03 | 1.09E−08 |
| 2F39 | 2.96E+05 | 1.37E−03 | 4.62E−09 | 2.84E+05 | 2.21E−03 | 7.79E−09 |
| 2F45 | 1.32E+05 | 2.88E−04 | 2.19E−09 | 1.42E+05 | 6.36E−04 | 4.48E−09 |
| 2F48 | 2.88E+05 | 0.002269 | 7.88E−09 | 2.95E+05 | 0.004377 | 1.48E−08 |
| Bay 2A8 | 1.36E+06 | 7.72E−03 | 5.68E−09 | no binding | no binding | no binding |
| Bay 2A8-K95L | 8.22E+05 | 3.99E−04 | 4.85E−10 | no binding | no binding | no binding |

TABLE 3

Binding constants
Binding constants ($k_a$, $k_d$, $K_D$) were obtained assuming a 1:1 interaction of human TFPIα or TFPI (1-79) and the antibody or Fab fragment of interest.

| | Human TFPIα | | | Human TFPI (1-79) | | |
|---|---|---|---|---|---|---|
| Compound | $k_a$ (1/Ms) | $k_d$ (1/s) | $K_D$ (M) | $k_a$ (1/Ms) | $k_d$ (1/s) | $K_D$ (M) |
| 0294 | 2.7E05 | 1.2E−04 | 4.6E−10 | 1.6E06 | 4.3E04 | 2.7E−10 |
| 0295 | 3.3E05 | 1.3E−04 | 4.1E−10 | n.d. | n.d. | n.d. |
| 0296 | 2.6E05 | 1.9E04 | 7.2E−10 | n.d. | n.d. | n.d. | n.d.: not determined.

Example 4: Antibody Binning

Competition between TFPI antibodies 1F91, 2F3, 2F22, 2F35, 2F45, Bay 2A8-K95L, MBS532510 (MyBioSource.com), and 10R-T141A (Fitzgerald Industries International) for binding to full-length TFPIα was measured using Bio-layer Interferometry (Fortebio Octet RED384 instrument, PALL Life Sciences). mAb 1F91, mAb 2F3, mAb 2F22, mAb 2F35, mAb 2F45, and Bay 2A8-K95L were randomly labelled with biotin on lysine residues using a 1:1.2 mol mAb:mol biotin-reagent (Thermo Scientific cat #21335) ratio and otherwise following the manufacturer's specifications. Biotin-labelled antibody was captured on streptavidin Fortebio sensortips (PALL Life Sciences) followed by binding of human TFPIα followed by binding of mAb 1F91, mAb 2F3, mAb 2F22, mAb 2F35, mAb 2F45, Bay 2A8-K95L, MBS532510 or 10R-T141A. Results are shown in Table 4 (The letter "X" signifies that mAbs compete for binding to TFPI. The symbol "✓" signifies that mAbs do not compete for binding to TFPI). These data show that the antibodies fall into 4 different bins, indicating that they have different binding epitopes. Bin 1: mAb 1F91, MBS532510, and 10R-T141A. Bin 2: mAb 2F3, 2F22 and 2F45. Bin 3: mAb 2F35. Bin 4: Bay2A8 K95L.

TABLE 4

Competition between the indicated TFPI antibodies for binding to TFPI

| | 2nd mAb | | | | | | | |
|---|---|---|---|---|---|---|---|---|
| 1st mAb | 1F91 | 2F3 | 2F22 | 2F35 | 2F45 | Bay2A8-K95L | MBS532510 | 10R-T141A |
| biotin-1F91 | X | X | X | ✓ | X | X | X | X |
| biotin-2F3 | X | X | X | ✓ | X | ✓ | X | X |
| biotin-2F22 | X | X | X | ✓ | X | ✓ | X | X |
| biotin-2F35 | ✓ | ✓ | ✓ | X | ✓ | ✓ | ✓ | ✓ |
| biotin-2F45 | X | X | X | ✓ | X | ✓ | X | X |
| biotin-Bay2A8-K95L | X | ✓ | ✓ | ✓ | ✓ | X | X | X |

Example 5: Effect of TFPI Antibodies Specific for TFPI (1-79) on TF-Induced Thrombin Generation in Human FVIII-Neutralised Plasma The effect of antibodies on thrombin generation was studied in normal human plasma (NHP, CryoCheck Normal Plasma). Initiation of coagulation was induced by re-calcification and addition of 1 µM TF with 4 µM phospholipid vesicles (PPP-Reagent low, Thrombinoscope). Haemophilia A-like plasma was obtained by the addition of 100 µg/ml sheep anti-human FVIII antibody (Haematologic Technologies Inc., PAHFVIII-S). Thrombin activity was assessed continuously following the conversion of the fluorogenic substrate Z-Gly-Gly-Arg-AMC.HCl (1-1140) from Bachem (Bubendorf, Switzerland). Fluorescence was measured in a microtiter plate Fluorskan Ascent fluorometer (Thermo Labsystems, Helsinki, Finland) with excitation and emission wavelengths set at 368 and 460 nm, respectively. A calibrator was used to allow calculation of the amount of thrombin formed and correction of the obtained relative fluorescence units for inner-filter effects and fluorogenic substrate consumption. In addition, the contribution to substrate conversion by thrombing α2-macroglobulin complexes was subtracted. These corrections were performed automatically by means of the calibrated automated thrombogram (CAT) computer software (version 5.0.0.745) provided by Thrombinoscope BV (Maastricht, the Netherlands). The first derivative of the data was taken that yielded the thrombin generation curve, allowing calculation of i) lag time, ii) total area under the curve, the endogenous thrombin potential (ETP), iii) thrombin peak height (Peak), iv) time to peak (ttPeak) and v) maximal rate of thrombin generation (Rate).

FIG. 1 (curve (a)) shows the thrombin generation curve with NHP. Addition of 100 µg/ml sheep anti-human FVIII antibody to NHP to simulate a haemophilia A-like condition strongly reduced thrombin generation (curve (b)). The suppression of thrombin generation as a result of neutralisation of FVIII was effectively reversed by the addition of 10 nM of TFPI-KPI-1 mAb 1F91 (curve (c)), mAb 2F3 (curve (d)), or mAb 2F22 (curve (e)). Parameters of thrombin peak height (Peak) and time to peak (ttPeak) derived from the curves in FIG. 1 and for additional TFPI (1-79) antibodies are listed in Table 5. The data shown in FIG. 1 and Table 5 suggest that 1) several TFPI (1-79) antibodies are inhibitory to TFPI activity, and 2) the individual inhibitory TFPI (1-79) antibodies increased thrombin peak height and decreased time to peak to a different extent.

Figure 2:
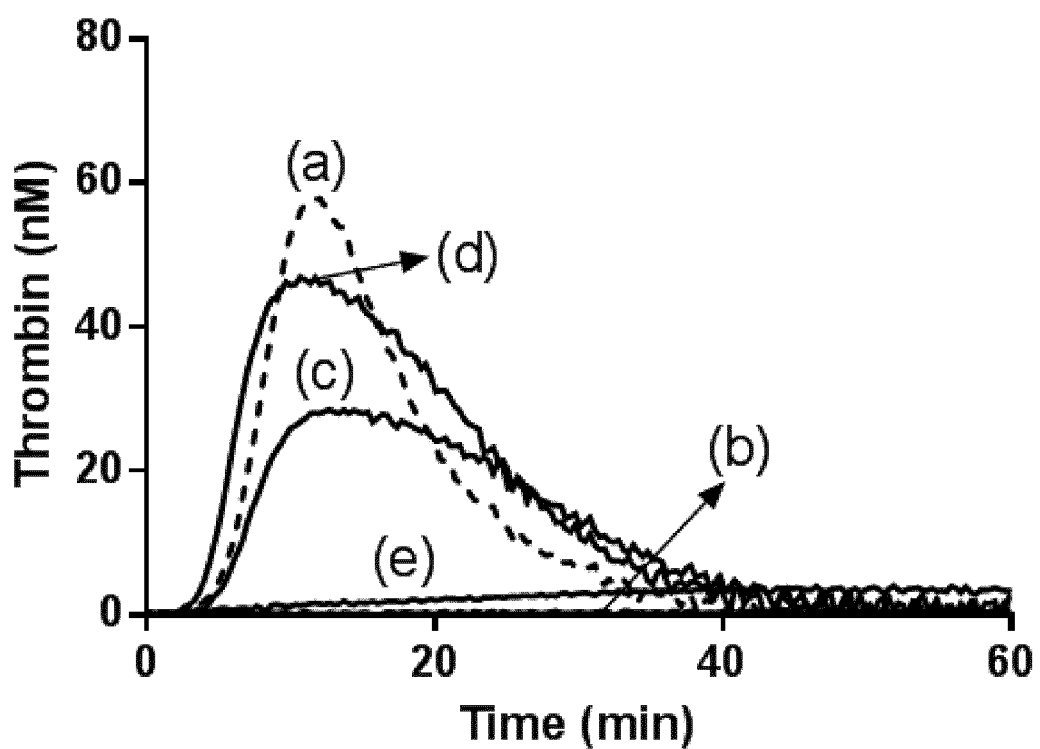

FIG. 2 (curve (a)) shows the thrombin generation curve with NHP. NHP contains about 1.6 nM TFPI, of which only about 0.2 nM is present as full length human TFPIα. FIG. 2 shows that addition of 5 nM full-length recombinant human TFPIα to FVIII-neutralised plasma completely prevented measurable thrombin generation (curve (b)). Addition of 10 nM of a high affinity antibody against KPI-1 (mAb 1F91) was completely incapable of establishing a significant thrombin generation in the presence of 5 nM TFPIα (curve (e)). Surprisingly, however, at these antibody concentrations mAb 2F22 (curve (d)) and to a lesser extent mAb 2F3 (curve (c)) could establish a robust thrombin generation that was comparable to thrombin generation in normal human plasma.

Parameters of thrombin peak height (Peak) and time to peak (ttPeak) derived from the curves in FIG. 2 and additional TFPI (1-79) mAbs are listed in Table 5. The data suggest that some but not all TFPI antibodies efficiently neutralise TFPI inhibition at conditions with elevated TFPI levels and re-establish thrombin generation to a level comparable to that of NHP. Similar results were found when selected antibodies (200 nM) were tested at an elevated TFPIα concentration of 20 nM (Table 6). TFPI antibody 2F22 was compared to different previously described TFPI antibodies (10R-T141A (Fitzgerald), MBS532510 (MyBioSource), ADG4903 (American Diagnostica GmbH), 2H8 (Mast et al., Arterioscler Thromb Vasc Biol. (2002) 22: 2099-2104)) for its ability to neutralise TFPI inhibition at elevated TFPI levels (20 nM). Parameters of thrombin generation are listed in Table 7 and the data show that TFPI antibody mAb 2F22 efficiently neutralises TFPI inhibition at elevated TFPI levels, whereas the previously described TFPI KPI-1 antibodies were not able to neutralize TFPI inhibition at these conditions. The mAb 2F22 was expressed as a chimeric antibody mAb 0294 and chimeric antibody fragments Fab 0295 and Fab 0296. The data in Table 8 shows that Fab fragment 0295 as a representative of mAb 0294/ mAb 2F22 (Fab 0295: SEQ ID: 17 and 20) retains high neutralising capacity of TFPI inhibition in FVIII neutralized plasma at normal or elevated TFPI levels.

TABLE 5

Thrombin peak height (Peak) and time to peak (ttPeak) derived from thrombin generation curves obtained in FVIII-neutralised plasma with or without 5 nM TFPIα

| FVIII neutralised plasma | | | |
|---|---|---|---|
| TFPI conc. (nM) | Compound (10 nM) | Peak (nM) | ttPeak (min) |
| 5 | 1F56 | 3.7 | 47.8 |
| 5 | 1F91 | 3.6 | 51.8 |
| 5 | 2F3 | 28.6 | 13.8 |
| 5 | 2F16 | 2.5 | 112.5 |
| 5 | 2F17 | 1.9 | 91.9 |
| 5 | 2F22 | 46.5 | 11.3 |
| 5 | 2F35 | 3.6 | 70.3 |
| 5 | 2F37 | 6.1 | 37.5 |
| 5 | 2F39 | 9.8 | 15.8 |
| 5 | 2F45 | 23.1 | 13.7 |
| 5 | 2F48 | 5.0 | 44.5 |
| 5 | — | 1.9 | 112.2 |
| 0 | 1F56 | 35.2 | 8.9 |
| 0 | 1F91 | 34.6 | 9.0 |
| 0 | 2F3 | 88.4 | 9.3 |
| 0 | 2F16 | 31.6 | 8.0 |
| 0 | 2F17 | 36.2 | 9.0 |
| 0 | 2F22 | 100.4 | 9.1 |
| 0 | 2F35 | 30.4 | 9.6 |
| 0 | 2F37 | 40.3 | 9.4 |
| 0 | 2F39 | 68.9 | 10.0 |
| 0 | 2F45 | 77.8 | 9.2 |
| 0 | 2F48 | 35.5 | 9.6 |
| 0 | — | 6.5 | 27.2 |

| | Peak (nM) | ttPeak (min) |
|---|---|---|
| Normal plasma | 59.1 | 11.4 |

TABLE 6

Thrombin peak height (Peak) and time to peak (ttPeak) derived from thrombin generation curves obtained in FVIII-neutralised plasma with 20 nM TFPIα

| FVIII neutralised plasma | | | |
|---|---|---|---|
| TFPI conc. (nM) | Compound (200 nM) | Peak (nM) | ttPeak (min) |
| 20 | 1F91 | 0.0 | n.a |
| 20 | 2F3 | 20.9 | 14.6 |
| 20 | 2F22 | 23.7 | 13.6 |
| 20 | 2F35 | 0 | n.a |

TABLE 6-continued

Thrombin peak height (Peak) and time to peak (ttPeak) derived from thrombin generation curves obtained in FVIII-neutralised plasma with 20 nM TFPIα

| | | | |
|---|---|---|---|
| 20 | 2F45 | 7.2 | 23.62 |
| 20 | — | 0 | n.a |

| | Peak (nM) | ttPeak (min) |
|---|---|---|
| Normal plasma | 71 | 11.6 |

TABLE 7

Thrombin peak height (Peak) and time to peak (ttPeak) derived from thrombin generation curves obtained in FVIII-neutralised plasma with 20 nM TFPIα

| FVIII neutralised plasma | | | |
|---|---|---|---|
| TFPI conc. (nM) | Compound (200 nM) | Peak (nM) | ttPeak (min) |
| 20 | 2F22 | 36.6 | 13.7 |
| 20 | 2H8 | 1.9 | 68.0 |
| 20 | AD4903 | 2.4 | 66.2 |
| 20 | 10R-T141A | 0 | n.a |
| 20 | MBS532510 | 0 | n.a |
| 20 | — | 0 | n.a |

| | Peak (nM) | ttPeak (min) |
|---|---|---|
| Normal plasma | 57.6 | 12.9 |

TABLE 8

Thrombin peak height (Peak) and time to peak (ttPeak) derived from thrombin generation curves obtained in FVIII-neutralised plasma with and without 20 nM TFPIα

| FVIII neutralised plasma | | | |
|---|---|---|---|
| TFPI conc. (nM) | Compound conc. (nM) | Peak (nM) Fab 0295 | ttPeak (min) Fab 0295 |
| 20 | 200 | 26.6 | 14.7 |
| 20 | 100 | 26.7 | 16.3 |
| 20 | 50 | 21.2 | 19.8 |
| 20 | 25 | 11.9 | 29.0 |
| 20 | 0 | 0.0 | n.a. |

| FVIII neutralised plasma | | | |
|---|---|---|---|
| TFPI conc. (nM) | Compound conc. (nM) | Peak (nM) 0295 | ttPeak (min) 0295 |
| 0 | 200 | 117.7 | 8.3 |
| 0 | 100 | 112.8 | 8.5 |
| 0 | 50 | 113.7 | 8.3 |
| 0 | 25 | 108.8 | 8.7 |
| 0 | 0 | 8.2 | 24.7 |

| | Peak (nM) | ttPeak (min) |
|---|---|---|
| Normal plasma | 61.1 | 13.8 |

Example 6: Crystal Structure of TFPI Kunitz Protease Inhibitor Domain 1 in Complex with a Fab Fragment of mAb 2F22

The 3D structure of the N-terminal part of human TFPI (1-79), which consists of an acidic N-terminal region and Kunitz-type Protease Inhibitor domain 1 (KPI-1) (SEQ ID NO: 2), in complex with a Fab fragment, Fab 0296 (SEQ ID NOs: 16 and 17) of mAb 2F22 was determined to high resolution using X-ray crystallography. The results demonstrate that the antibody is capable of binding the KPI-1 of TFPI, and part of the preceding N-terminal. The resulting human TFPI epitope residues comprise Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 (SEQ ID NO: 2).

Materials and Methods

For crystallographic purpose CMV promoter-based expression vectors (pTT vectors) were generated for transient expression of the Fab fragment corresponding to mAb 2F22 antibody fragment for crystallography as described in Example 2.

The Fab fragment of mAb 2F22 was expressed in a murine-human chimeric form Fab 0296 (SEQ ID NO: 16 and 17) in EXPI293F cells and purified by standard affinity chromatography using KappaSelect resin as described in example 2.

Human TFPI KPI-1, including the N-terminal part of human TFPI, and, additionally, a GSSGSSG tag N-terminally attached (SEQ ID NO: 18) and Fab 0296 which consists of a light chain corresponding to SEQ ID NO: 17 and a heavy chain fragment corresponding to SEQ ID NO: 16, both in phosphate buffered saline (PBS) buffer (4 tablets in 2 litres of water, GIBCO Cat. No. 18912-014 Invitrogen Corporation), were mixed with a slight molar excess (1.1:1) of the TFPI species. The complex was then concentrated to about 10.0 mg/ml using an Amicon Ultra-4 centrifugal filter with a 10,000 Da molecular weight cut-off. Crystals were grown by the sitting drop-technique using a 96 wells TTP IQ plate from TTP Lab Tech no: 4150-05800 and 100 μl precipitant solution per well. The precipitant solution contained 20% w/v PEG 3350, 200 mM potassium formate and was mixed with the protein solution in a ratio of 3:1. Initial total drop size was 200 nl and crystals appeared after a few days. A crystal was prepared for cryo-freezing by transferring 1 μl of a cryo-solution mix containing 75% of the precipitant solution and 25% glycerol to the drop containing the crystal. The soaking was allowed for about 2 minutes. The crystal was then fished, flash frozen in liquid $N_2$ and kept at a temperature of 100 K by a cryogenic $N_2$ gas stream during data collection. Crystallographic data were collected, to 1.65 Å resolution at beam-line BL911-3 at MAX-lab, Lund, Sweden. Space group determination, integration and scaling of the data were made by the XDS software package [Kabsch, W., J. Appl. Crystallogr., (1993), Vol. 26, pages 795-800]. The space group was determined to be C2 and the cell parameters for the synchrotron data were determined to be 89.010, 66.660, 106.110 Å, respectively, and with a β angle of 111.18°. The R-sym to 1.65 Å resolution was 8.4% and completeness 99.5%. Mean of intensity/sigma(intensity) of unique reflections were equal to 2.0 at around 1.8 Å resolution.

The molecular replacement (MR) method was used for structure determination using the coordinates of a Fab molecule with accession code 1 NGZ [Yin, J. et al, Proc Natl Acad Sci USA. 2003 Feb. 4, (100), Vol. 100 pages 856-861]

of the Protein Data Bank (PDB) [Berman, H. M. et al, Nucleic Acids Res., (2000), Vol. 28, pages 235-242]. The Fab molecule was divided into two domains, the variable and the constant domains, which each was used as search model in the MR calculations. The Molrep software [Vagin, A. et al, J. Appl. Crystallogr., (1997), Vol. 30, pages 1022-1025] of the CCP4 package CCP4 [Collaborative Computational Project, N., Acta crystallographica. Section D, Biological crystallography, (1994), Vol. 50, pages 760-763] was used to find the positions of the constant and variable Fab domains. The KPI-1 domain was not found in the MR step, however, the difference electron density map indicated the approximate positions of the KPI-1 domain molecules at this stage. Electron density improvements by the DM software of the CCP4 software package, followed by automated model building and phase improvements using the ARP-wARP software [Langer, G. et al, Nat Protoc, (2008), Vol. 3, pages 1171-1179][Murshudov, G. N. et al, Acta Crystallographica Section D Biological Crystallography, (2011), Vol. 67, pages 355-367] gave an almost complete structure of both the Fab 0296 molecule and of the KPI-1 domain structure, and part of the N-terminal preceding the KPI-1 domain. For the TFPI (SEQ ID NO: 2) residues from 15 to 77 are included in the X-ray model which in addition to the KPI-1 domain also includes some residues N-terminally of KPI-1 (residues 26-76). For the Fab 0296 fragment the light chain residues 1 to 212 and the heavy chain residues 1 to 221 are observed. A procedure of computer graphics inspection of the electron density maps, model corrections and building using the Coot software program [Emsley, P. et al, Acta Crystallogr. Sect. D—Biol. Crystallogr., (2004), Vol. 60, pages 2126-2132] followed by crystallographic refinements, using the software programs Refmac5 [Murshudov, G. N. et al, Acta Crystallographica Section D Biological Crystallography, (2011), Vol. 67, pages 355-367] of the CCP4 software package was entered. The procedure was cycled until no further significant improvements could be made to the model. Final R- and R-free for all data to 1.65 Å resolution were 0.192 and 0.220, respectively.

Results

Calculation of the average areas excluded in pair-wise interactions by the software program Areaimol [Lee, B. et al, J Mol Biol, (1971), Vol. 55, pages 379-400][Saff, E. B. et al, Math Intell, (1997), Vol. 19, pages 5-11] of the CCP4 program suite [Collaborative Computational Project, N., Acta crystallographica. Section D, Biological crystallography, (1994), Vol. 50, pages 760-763] gave for the human TFPI fragment/anti-TFPI2F22 Fab molecular complex of the crystal structure 1195 Å$^2$.

The direct contacts between the TFPI KPI-1, inclusive the N-terminal part of TFPI observed in the crystal structure, (SEQ ID NO: 2) and Fab 0296 (SEQ ID NOs: 16 and 17), were identified by running the Contacts software of the CCP4 program suite [Bailey, S., Acta Crystallogr. Sect. D—Biol. Crystallogr., (1994), Vol. 50, pages 760-763] using a cut-off distance of 4.0 Å between the Fab 0296 and the TFPI fragment molecules. The results from the soluble TFPI fragment/Fab 0296 complex crystal structure are shown in Table 9.

The resulting TFPI KPI-1, including the TFPI N-terminal region, epitope for Fab 0296 was found to comprise the following residues of TFPI (using sequence numbering as of SEQ ID NO: 2): Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75. Evaluated from distances, charge-charge interactions, hydrogen bonds, polar and hydrophobic interactions and low solvent accessibility the following residues seems to be particularly important residues of the epitope: Arg 41, Arg 65 and Glu 67 (SEQ ID NO. 2).

Thus, the TFPI epitope of mAb 2F22 (represented by Fab 0296) comprises residues preceding the KPI-1 domain, including a short N-terminal α-helix, residues in the loop before β-strands 1 of the KPI-1 domain and residues in the beginning of β-strand 1. It also includes residues in the end of β-strand 2 and residues in the loop between β-strand 2 and the C-terminal α-helix of KPI-1 and residues within the C-terminal α-helix of KPI-1.

Hence, the results show that Fab 0296, and thus mAb 2F22 specifically binds to TFPI KPI-1 and part of the preceding N-terminal region.

The Fab 0296 paratope for TFPI KPI-1, includes residues Val 2, Phe 27, Tyr 32, Trp 52, Arg 53, Gly 54, Gly 55, Ser 56, Ile 57, Asp 58, Tyr 59, Ala 61, Met 64, Lys 97, Ser 99, His 100, Asn 102, Tyr 103, Val 104, Gly 105 and Tyr 106 of the heavy (H) chain (SEQ ID NO: 16, Table 9), and residues Pro 31, Ala 32, Tyr 49, Ser 50, Asn 53, Tyr 55, Thr 56, Tyr 91, Thr 92, Ser 93 and Tyr 94 of the light (L) chain (SEQ ID NO: 17, Table 9).

TABLE 9

Data from TFPI fragment/Fab 0296 complex crystal structure TFPI KPI-1, chain K, (SEQ ID NO: 2) interactions with the heavy chain (chain H) of Fab 0296 (SEQ ID NO: 16) and light chain (chain L) of Fab 0296 (SEQ ID NO: 17) for the crystallographic complex. A distance cut-off of 4.0 Å was used. The contacts were identified by the CONTACT computer software program of the CCP4 suite [Collaborative Computational Project, N., Acta crystallographica.Section D, Biological crystallography, (1994), Vol. 50, pages 760-763].
Hydrogen-bonds are specific between a donor and an acceptor, are typically strong, and are easily identifiable.

| Human TFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| Leu | 16K | CB | Tyr | 32H | OH | 3.77 | |
| Leu | 16K | CD1 | Phe | 27H | CB | 3.99 | |
| | | | Tyr | 32H | CZ | 3.78 | |
| | | | Tyr | 32H | CE2 | 3.86 | |
| | | | Tyr | 32H | OH | 3.40 | |
| | | | Lys | 97H | CE | 3.77 | |
| Leu | 16K | CD2 | Val | 2H | CG2 | 3.74 | |
| Pro | 17K | CG | Thr | 56L | OG1 | 3.68 | |
| Leu | 19K | CA | Tyr | 49L | OH | 3.80 | |
| Leu | 19K | CB | His | 100H | ND1 | 3.95 | |
| | | | His | 100H | CE1 | 3.46 | |
| | | | His | 100H | NE2 | 3.73 | |
| | | | Tyr | 49L | OH | 3.79 | |
| Leu | 19K | CD1 | Ser | 99H | O | 3.47 | |
| | | | His | 100H | CD2 | 3.85 | |
| | | | His | 100H | NE2 | 3.69 | |
| | | | Tyr | 55L | CE1 | 3.86 | |
| Leu | 19K | C | Tyr | 49L | OH | 3.85 | |
| Lys | 20K | N | Tyr | 49L | CZ | 3.89 | |
| | | | Tyr | 49L | OH | 3.01 | *** |
| Lys | 20K | CA | Tyr | 49L | OH | 3.93 | |
| Lys | 20K | CB | Tyr | 49L | OH | 3.70 | |
| Lys | 20K | CG | Tyr | 49L | OH | 3.51 | |
| Lys | 20K | CD | Tyr | 49L | OH | 3.80 | |
| | | | Asn | 53L | CG | 3.73 | |
| | | | Asn | 53L | OD1 | 3.29 | |
| Lys | 20K | CE | Asn | 53L | OD1 | 3.93 | |
| Lys | 20K | C | His | 100H | CE1 | 3.92 | |
| Lys | 20K | O | His | 100H | ND1 | 3.41 | * |
| | | | His | 100H | CE1 | 2.88 | |
| | | | Tyr | 49L | CE2 | 3.58 | |

TABLE 9-continued

Data from TFPI fragment/Fab 0296 complex crystal structure TFPI KPI-1, chain K, (SEQ ID NO: 2) interactions with the heavy chain (chain H) of Fab 0296 (SEQ ID NO: 16) and light chain (chain L) of Fab 0296 (SEQ ID NO: 17) for the crystallographic complex. A distance cut-off of 4.0 Å was used. The contacts were identified by the CONTACT computer software program of the CCP4 suite [Collaborative Computational Project, N., Acta crystallographica.Section D, Biological crystallography, (1994), Vol. 50, pages 760-763].
Hydrogen-bonds are specific between a donor and an acceptor, are typically strong, and are easily identifiable.

| Human TFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| Leu | 21K | CA | Tyr | 106H | OH | 3.73 |
| Leu | 21K | CB | Tyr | 106H | OH | 3.99 |
| Leu | 21K | CD2 | Tyr | 103H | CE2 | 3.72 |
| | | | Tyr | 103H | CD2 | 3.52 |
| | | | His | 100H | ND1 | 3.89 |
| | | | Tyr | 106H | OH | 3.87 |
| Leu | 21K | C | Tyr | 106H | OH | 3.71 |
| Met | 22K | N | Tyr | 106H | CZ | 3.81 |
| | | | Tyr | 106H | OH | 2.81 | *** |
| | | | Tyr | 106H | CE2 | 3.87 |
| Met | 22K | CA | Tyr | 106H | OH | 3.68 |
| Met | 22K | CB | Tyr | 106H | OH | 3.60 |
| Met | 22K | CG | Ser | 50L | OG | 3.75 |
| Met | 22K | SD | Pro | 31L | CG | 3.78 |
| Met | 22K | CE | Pro | 31L | CG | 3.80 |
| Met | 22K | O | Tyr | 106H | OH | 3.86 | * |
| Phe | 25K | CZ | Gly | 105H | O | 3.58 |
| | | | Ala | 32L | CB | 3.89 |
| Phe | 25K | CE2 | Val | 104H | O | 3.96 |
| | | | Gly | 105H | CA | 3.87 |
| | | | Gly | 105H | C | 3.87 |
| | | | Gly | 105H | O | 3.41 |
| | | | Tyr | 106H | CE1 | 3.90 |
| | | | Tyr | 106H | CZ | 3.61 |
| | | | Tyr | 106H | OH | 3.79 |
| | | | Tyr | 106H | CE2 | 3.86 |
| Phe | 25K | CD2 | Val | 104H | O | 3.81 |
| | | | Tyr | 106H | CZ | 3.81 |
| | | | Tyr | 106H | OH | 3.59 |
| Cys | 35K | SG | Ala | 61H | CB | 3.72 |
| Ala | 37K | CB | Met | 64H | CE | 3.75 |
| Met | 39K | SD | Ile | 57H | O | 3.21 |
| Met | 39K | CE | Ser | 56H | CA | 3.87 |
| | | | Ser | 56H | CB | 3.66 |
| | | | Ile | 57H | N | 3.44 |
| | | | Ile | 57H | O | 3.31 |
| Arg | 41K | NE | Ser | 56H | CB | 3.74 |
| Arg | 41K | CZ | Ser | 56H | CB | 3.85 |
| | | | Asp | 58H | OD1 | 3.00 |
| Arg | 41K | NH1 | Asp | 58H | CG | 3.53 |
| | | | Asp | 58H | OD1 | 2.67 | *** |
| | | | Asp | 58H | OD2 | 3.65 | * |
| Arg | 41K | NH2 | Ser | 56H | CB | 3.50 |
| | | | Ile | 57H | N | 3.79 | * |
| | | | Ile | 57H | C | 3.58 |
| | | | Ile | 57H | O | 3.12 | *** |
| | | | Asp | 58H | CG | 3.78 |
| | | | Asp | 58H | OD1 | 2.58 | *** |
| Tyr | 56K | CE2 | Asp | 58H | OD1 | 3.40 |
| Gly | 57K | O | Met | 64H | CE | 3.82 |
| Gly | 58K | O | Asp | 58H | C | 3.65 |
| | | | Tyr | 59H | N | 2.83 | *** |
| | | | Tyr | 59H | CB | 3.96 |
| | | | Tyr | 59H | CD1 | 3.80 |
| | | | Asp | 58H | CA | 3.56 |
| | | | Tyr | 59H | CA | 3.82 |
| | | | Tyr | 59H | O | 3.69 | * |
| Cys | 59K | CA | Tyr | 59H | O | 3.61 |
| Cys | 59K | CA | Tyr | 59H | O | 3.59 |
| Cys | 59K | CB | Tyr | 59H | O | 3.52 |
| Cys | 59K | CB | Tyr | 59H | O | 3.30 |
| Cys | 59K | SG | Met | 64H | SD | 3.34 |
| | | | Ala | 61H | CA | 3.60 |
| | | | Tyr | 59H | O | 3.92 |
| | | | Ala | 61H | N | 3.94 |
| | | | Ala | 61H | CB | 3.75 |
| Cys | 59K | SG | Ala | 61H | CB | 3.85 |
| Glu | 60K | N | Ser | 93L | O | 3.90 | * |
| Glu | 60K | CA | Ser | 93L | O | 3.25 |
| | | | Ser | 93L | CB | 4.00 |
| | | | Ser | 93L | C | 3.99 |
| Glu | 60K | OE2 | Tyr | 94L | CE1 | 3.99 |
| Glu | 60K | C | Ser | 93L | O | 3.30 |
| Glu | 60K | O | Ser | 93L | O | 3.25 | *** |
| Gly | 61K | O | Ser | 93L | CA | 3.27 |
| | | | Ser | 93L | CB | 3.51 |
| Asn | 62K | CA | Thr | 92L | O | 3.84 |
| Gln | 63K | CA | Val | 104H | CG1 | 3.96 |
| Gln | 63K | CG | Tyr | 91L | O | 3.58 |
| | | | Gly | 105H | CA | 3.77 |
| Gln | 63K | CD | Tyr | 91L | O | 3.77 |
| | | | Thr | 92L | CA | 3.83 |
| Gln | 63K | OE1 | Thr | 92L | O | 3.95 | * |
| | | | Thr | 92L | CA | 3.87 |
| Gln | 63K | NE2 | Tyr | 91L | O | 3.65 | * |
| | | | Thr | 92L | CA | 3.98 |
| | | | Thr | 92L | CG2 | 3.73 |
| | | | Ala | 32L | CB | 3.74 |
| Arg | 65K | NE | Asp | 58H | OD1 | 3.91 | * |
| | | | Asp | 58H | OD2 | 3.76 | * |
| Arg | 65K | CZ | Asp | 58H | OD2 | 3.81 |
| Arg | 65K | NH2 | Asp | 58H | CG | 3.65 |
| | | | Asp | 58H | OD2 | 2.92 | *** |
| | | | Val | 104H | CG1 | 3.71 |
| | | | Val | 104H | CG2 | 3.60 |
| Arg | 65K | O | Val | 104H | CG2 | 3.64 |
| Phe | 66K | CD1 | Tyr | 103H | CE1 | 3.80 |
| | | | Tyr | 103H | CD1 | 3.77 |
| Phe | 66K | CE1 | Tyr | 103H | CE1 | 3.74 |
| | | | Tyr | 103H | CD1 | 3.63 |
| Glu | 67K | CB | Asn | 102H | ND2 | 3.46 |
| Glu | 67K | CG | Ser | 56H | OG | 3.33 |
| Glu | 67K | CD | Gly | 54H | N | 3.40 |
| | | | Gly | 54H | CA | 3.69 |
| | | | Ser | 56H | OG | 3.32 |
| | | | Trp | 52H | CB | 3.78 |
| | | | Asn | 102H | ND2 | 3.94 |
| | | | Ser | 56H | CB | 3.89 |
| Glu | 67K | OE1 | Gly | 54H | N | 2.79 | *** |
| | | | Gly | 54H | CA | 3.49 |
| | | | Trp | 52H | CB | 3.57 |
| | | | Trp | 52H | C | 3.94 |
| | | | Arg | 53H | N | 3.47 | * |
| | | | Arg | 53H | CG | 3.98 |
| | | | Arg | 53H | CD | 3.87 |
| | | | Arg | 53H | C | 3.84 |
| | | | Asn | 102H | CG | 3.86 |
| | | | Asn | 102H | OD1 | 3.93 | * |
| | | | Asn | 102H | ND2 | 2.97 | *** |

TABLE 9-continued

Data from TFPI fragment/Fab 0296 complex crystal structure TFPI KPI-1, chain K, (SEQ ID NO: 2) interactions with the heavy chain (chain H) of Fab 0296 (SEQ ID NO: 16) and light chain (chain L) of Fab 0296 (SEQ ID NO: 17) for the crystallographic complex. A distance cut-off of 4.0 Å was used. The contacts were identified by the CONTACT computer software program of the CCP4 suite [Collaborative Computational Project, N., Acta crystallographica.Section D, Biological crystallography, (1994), Vol. 50, pages 760-763].
Hydrogen-bonds are specific between a donor and an acceptor, are typically strong, and are easily identifiable.

| Human TFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| Glu | 67K | OE2 | Gly | 54H | C | 3.27 | |
| | | | Gly | 54H | O | 3.77 | * |
| | | | Gly | 55H | N | 3.51 | * |
| | | | Ser | 56H | N | 3.02 | *** |
| | | | Gly | 54H | N | 3.28 | *** |
| | | | Gly | 54H | CA | 3.27 | |
| | | | Ser | 56H | CA | 3.64 | |
| | | | Ser | 56H | OG | 2.52 | *** |
| | | | Trp | 52H | CB | 3.91 | |
| | | | Ser | 56H | CB | 3.10 | |
| Glu | 71K | CD | Asn | 102H | ND2 | 3.46 | |
| | | | Arg | 53H | NH1 | 3.50 | |
| Glu | 71K | OE1 | Asn | 102H | CB | 3.82 | |
| | | | Asn | 102H | CG | 3.79 | |
| | | | Asn | 102H | ND2 | 2.81 | *** |
| Glu | 71K | OE2 | Arg | 53H | NH2 | 3.78 | * |
| | | | Arg | 53H | CD | 3.65 | |
| | | | Arg | 53H | NE | 3.58 | * |
| | | | Asn | 102H | ND2 | 3.43 | * |
| | | | Arg | 53H | CZ | 3.01 | |
| | | | Arg | 53H | NH1 | 2.28 | *** |
| Glu | 71K | O | Tyr | 103H | CE1 | 3.91 | |
| | | | Tyr | 103H | OH | 3.57 | * |
| Met | 75K | N | Tyr | 103H | OH | 3.80 | * |
| Met | 75K | CB | Tyr | 103H | CE1 | 3.82 | |
| | | | Tyr | 103H | CZ | 4.00 | |
| | | | Tyr | 103H | OH | 3.73 | |

In the last column "***" indicates a strong possibility for a hydrogen bond at this contact (distance <3.3 Å) as calculated by CONTACT,
"*" indicates a weak possibility (distance >3.3 Å).
Blank indicates that the program considered there to be no possibility of a hydrogen bond.

Example 7: Effect of TFPI Antibodies Specific for TFPI (1-79) on the Affinity for TFPI to FXa and on the Affinity for TFPI to FVIIa/Soluble TF Measured by Surface Plasmon Resonance The ability of TFPI antibodies to inhibit the interaction between TFPI and FXa or TFPI and FVIIa/soluble TF (FVIIa/sTF) was evaluated using an SPR assay with the Biacore T200 instrument. The affinity for FXa or FVIIa/sTF to TFPI bound to a TFPI KPI-1 antibody was compared to the affinity for FXa or FVIIa/sTF to TFPI bound to TFPI KPI-3 mAb 4F110 (WO2012/001087). As a control the affinity for FXa or FVIIa/sTF to TFPI bound to TFPI KPI-2 mAb 4F36 (WO2010/072691) was included in the assay.

Polyclonal rabbit anti-mouse immunoglobulin (Mouse Antibody Capture Kit, GE Healthcare) was immobilized to a series S CM4 sensor chip (GE Healthcare) in flow-cells 1-4 as described in example 3. For every experiment, the relevant anti-TFPI N-terminal antibodies (2F22, 2F3, 2F45, 2F48, 1F91, 2F35, 10R-T141A (Fitzgerald), MBS532510 (MyBioSource), ADG4903 (American Diagnostica GmbH), 2H8 (Mast et al., Arterioscler Thromb Vasc Biol. (2002) 22: 2099-2104)), anti-TFPI KPI-2 antibody (4F36, WO2010/072691) or anti-TFPI KPI-3 antibody (4F110 disclosed in WO2012/001087) mAb was injected for 180 sec in flow cell 2, 3 or 4 at 10 μl/min flow rate, followed by a subsequent injection of 20 nM human TFPIα (SEQ ID NO: 1) for 180 sec in all flow cells (1-4) at 10 μl/min flow rate. Different concentrations (25 nM, 12.5 nM, 6.25 nM and 0 nM) of FXa (Haematologic Technologies) were tested by diluting the sample in running buffer (10 mM HEPES, pH 7.4, 150 mM NaCl, 10 mM $CaCl_2$, 0.05% Surfactant P20, 1 mg/ml BSA). Each sample was assayed using 120 seconds of contact time followed by 180 seconds of dissociation time at 30 μl/min flow rate. The sensor surface was regenerated with 10 mM Glycine pH 1.7 with two cycles each of 30 seconds at 30 μl/min flow rate. Each sample of FVIIa was prepared at a final concentration of 320 nM, 160 nM, 80 nM or 0 nM in running buffer containing 620 nM sTF. Soluble tissue factor 1-219 (sTF) was prepared according to published procedures (Freskgard et al., 1996). Expression and purification of recombinant FVIIa was performed as described previously (Thim et al., 1988; Persson and Nielsen, 1996). The FVIIa/sTF complex was incubated at room temperature for 10-15 min before initiation of the first sample injection. Each sample was assayed using 120 seconds of contact time followed by 180 seconds of dissociation time at 30 μl/min flow rate. The sensor surface was regenerated with 10 mM Glycine pH 1.7 with two cycles each of 30 seconds at 30 μl/min flow rate. Biacore T200 Evaluation software (version 2.0) was used to analyse the data. Determination of binding constants ($k_a$, $k_d$, $K_D$) was obtained assuming a 1:1 interaction of TFPI and FXa or TFPI and FVIIa/sTF.

Some anti-TFPI antibodies specific to TFPI (1-79) (mAbs 2F22, 2F3 and 2F45) decreased the affinity for TFPI to FXa more than 30-fold compared to the affinity for FXa to TFPI bound to anti-TFPI KPI-3 mAb 4F110, whereas all other tested antibodies had no or only a minor (less than 10-fold) effect on the affinity for FXa to TFPI (Table 10). The decrease in affinity was primarily due to a faster off-rate ($k_d$).

All anti-TFPI antibodies specific to TFPI (1-79) blocked binding of TFPI to FVIIa/sTF (Table 11).

TABLE 10

The affinity of FXa to human TFPIα bound to the indicated antibody was measured by SPR analysis. Determination of binding constants ($k_a$, $k_d$, $K_D$) was obtained assuming a 1:1 interaction of human TFPIα and FXa

| Sample | Compound | TFPI epitope | $k_a$ (1/Ms) | $k_d$ (1/s) | $K_D$ (M) |
|---|---|---|---|---|---|
| FXa | 4F110 | KPI-3 | 5.67E+05 | 1.67E−04 | 2.95E−10 |
| FXa | 4F36 | KPI-2 | 1.85E+06 | 5.52E−02 | No binding |
| FXa | 2F22 | 1-79 | 1.95E+05 | 1.31E−02 | 6.74E−08 |
| FXa | 2F3 | 1-79 | 1.79E+05 | 2.33E−02 | 1.30E−07 |
| FXa | 2F45 | 1-79 | 2.76E+06 | 3.21E−02 | 1.16E−08 |
| FXa | 2F48 | 1-79 | 6.99E+05 | 1.67E−03 | 2.39E−09 |
| FXa | 1F91 | 1-79 | 6.62E+05 | 1.20E−03 | 1.81E−09 |
| FXa | 2F35 | 1-79 | 6.17E+05 | 1.34E−03 | 2.16E−09 |
| FXa | 10R-T141A | 1-79 | 8.10E+05 | 1.18E−03 | 1.46E−09 |
| FXa | MBS532510 | 1-79 | 1.09E+06 | 1.19E−03 | 1.09E−09 |
| FXa | ADG4903 | 1-79 | 9.34E+05 | 1.06E−03 | 1.14E−09 |
| FXa | 2H8 | 1-79 | 7.77E+05 | 9.53E−04 | 1.23E−09 |

TABLE 11

The affinity of FVIIa/sTF to human TFPIα bound to the indicated antibody was measured by SPR analysis. Determination of binding constants ($k_a$, $k_d$, $K_D$) was obtained assuming a 1:1 interaction of human TFPIα and the FVIIa/sTF complex.

| Sample | Compound | TFPI epitope | $k_a$ (1/Ms) | $k_d$ (1/s) | $K_D$ (M) |
|---|---|---|---|---|---|
| FVIIa/sTF (640 nM) | 4F110 | KPI-3 | 2.31E+04 | 4.61E−03 | 1.99E−07 |
| FVIIa/sTF (640 nM) | 4F36 | KPI-2 | 1.09E+04 | 2.79E−03 | 2.56E−07 |
| FVIIa/sTF (640 nM) | 2F22 | 1-79 | n.b. | n.b | n.b. |
| FVIIa/sTF (640 nM) | 2F3 | 1-79 | n.b. | n.b | n.b. |
| FVIIa/sTF (640 nM) | 2F45 | 1-79 | n.b. | n.b | n.b. |
| FVIIa/sTF (640 nM) | 2F48 | 1-79 | n.b. | n.b | n.b. |
| FVIIa/sTF (640 nM) | 1F91 | 1-79 | n.b. | n.b | n.b. |
| FVIIa/sTF (640 nM) | 2F35 | 1-79 | n.b. | n.b | n.b. |
| FVIIa/sTF (640 nM) | 10R-T141A | 1-79 | n.b. | n.b | n.b. |
| FVIIa/sTF (640 nM) | MBS532510 | 1-79 | n.b. | n.b | n.b. |
| FVIIa/sTF (640 nM) | ADG4903 | 1-79 | n.b. | n.b | n.b. |
| FVIIa/sTF (640 nM) | 2H8 | 1-79 | n.b. | n.b | n.b. | n.b.: no detectable binding

Example 8: Effect of Anti-TFPI Antibodies Specific to TFPI (1-79) on TFPIα Inhibition of FXa Amidolytic Activity The effect of antibodies on TFPIα inhibition of FXa (Enzyme Research Laboratories Ltd.) amidolytic activity towards the chromogenic substrate S-2765 (Chromogenix) was assayed in buffer containing 50 mM HEPES, pH 7.4, 100 mM NaCl, 5 mM $CaCl_2$, 0.1 mg/ml BSA. Anti-TFPI mAb (32 nM) was incubated with 8 nM TFPIα (SEQ ID NO: 1) for 30 min at room temperature. S-2765 (0.5 mM) was added and incubated for 5 min. Reactions were initiated by addition of FXa to final a concentration of 0.1 nM. Product formation was measured after 40 min incubation at 405 nM in a Spectramax 340 Microplate spectrophotometer. The activity in the absence of TFPIα was set to 100% and the activity in the presence of TFPIα, but absence of antibody, was set to 0%. The results are shown in Table 12. As expected, pre-incubation of TFPIα with KPI-2 mAb2021 (disclosed in WO2010/072691) completely neutralized TFPIα activity towards FXa. The effect of TFPI KPI-1 antibodies could be divided into two groups, one group (2F3, 2F22, 2F45) which partially neutralized TFPIα inhibition of FXa (>20%) and another group, which did not affect TFPIα inhibition of FXa appreciably (<20%).

TABLE 12

Effect of antibodies on TFPIα inhibition of FXa
Remaining FXa activity measured after 40 min incubation with TFPIα. The activity in the absence of TFPIα was set to 100% and the activity in the presence of TFPIα, but absence of antibody, was set to 0%.

| Compound | FXa activity (%) |
|---|---|
| 2021 | 103.8 ± 6.6 |
| 1F56 | 5.5 ± 1.1 |
| 1F91 | 5.8 ± 2.1 |
| 2F3 | 48.9 ± 1.3 |
| 2F22 | 50.4 ± 1.4 |
| 2F35 | 13.4 ± 8.0 |
| 2F45 | 28.2 ± 1.8 |
| 2F48 | 8.2 ± 1.9 |
| 2H8 | 3.4 |
| ADG4903 | 4.9 |
| 10R-T141A | 6.8 |
| MBS532510 | 6.8 |

Example 9: Reversal of TFPIα Inhibition by Anti-TFPI Antibodies Specific to TFPI (1-79) Measured by sTF/FVIIa- and FXa Amidolytic Activities The effect of antibodies on TFPIα inhibition of FVIIa/sTF activity was studied in 20 mM HEPES, pH 7.5, 150 mM NaCl 5 mM $CaCl_2$ 0.1% BSA. The reaction mixture contained 5 nM FVIIa, 10 nM soluble TF (sTF) and 0.5 mM of the chromogenic substrate S-2288 (H-D-Ile-Pro-Arg-pNa, Chromogenix). Soluble tissue factor 1-219 (sTF) was prepared according to published procedures (Freskgard et al., 1996). Expression and purification of recombinant FVIIa was performed as described previously (Thim et al., 1988; Persson and Nielsen, 1996). The activity was measured at room temperature by the change in $OD_{405\ nm}$, and the activity in absence of TFPI was set to 100%. The FVIIa/sTF activity was inhibited by the addition of 150 nM TFPIα (SEQ ID NO: 1), and inhibition was reversed by 200 nM of various antibodies against TFPI (1-79) as shown in Table 13. Some antibodies against TFPI (1-79) (1F91, 2F3, 2F22, 2F45) reversed TFPIα inhibition of FVIIa/sTF under these conditions. One TFPI (1-79) antibody (2F35) and the KPI-2 antibody (2021 disclosed in WO2010/072691) were without an appreciable effect.

Next the effect of KPI-1 antibodies on reversal of TFPIα inhibition of FXa activity was studied. The reaction mixture contained 1 nM FXa, and 0.5 mM of the chromogenic substrate S-2765 (Z-D-Arg-Gly-Arg-pNa, Chromogenix) in 20 mM HEPES pH 7.5, 150 mM NaCl, 5 mM $CaCl_2$, 0.1% BSA. FXa was incubated with 4 nM TFPIα (SEQ ID NO: 1) for 15 min followed by addition of 0.5 mM S-2765. The activity was then measured at room temp by the change in $OD_{405\ nm}$. Reversal of inhibition was induced after 15 min by addition of 20 nM TFPI (1-79) (1F91, 2F3, 2F22, 2F35, 2F45) or KPI-2 (2021 disclosed in WO2010/072691) antibody. The resulting progress curve was followed and the slope was measured 100 min after antibody addition. The activity in absence of TFPI was set to 100%. The results are shown in Table 13. Since KPI-2 binds to FXa, it was surprising that a number of anti-TFPI antibodies specific to TFPI (1-79) (2F3, 2F22, 2F45) more efficiently reversed TFPIα inhibition of FXa activity than mAb 2021 which binds to an epitope on KPI-2 which interacts with the FXa active site. The results suggest that areas on TFPI (1-79), other than the primary contact area on KPI-2, are crucial for the binding of TFPIα to FXa.

TABLE 13

Reversal of TFPIα inhibition of FVIIa/sTF and FXa amidolytic activity

| Compound | FVIIa/sTF activity (%) | FXa activity (%) after 100 min incubation |
|---|---|---|
| FVIIa/sTF or FXa (A) | 100 ± 0.7 | 100 ± 1.7 |
| (A) + TFPI (B) | 59.0 ± 0.2 | 0.5 ± 0.06 |
| (B) + 1F91 | 82.2 ± 0.4 | 5.1 ± 0.06 |
| (B) + 2F3 | 88.6 ± 0.5 | 58.1 ± 1.0 |
| (B) + 2F22 | 88.3 ± 0.5 | 60.8 ± 1.5 |
| (B) + 2F35 | 61.4 ± 0.2 | 4.2 ± 0.1 |
| (B) + 2F45 | 87.5 ± 0.4 | 38.3 ± 1.9 |
| (B) + 2021 | 66.5 ± 0.3 | 18.6 ± 0.4 |

Example 10: Effect of Antibodies Specific to TFPI (1-79) on FXa Generation

The effect of anti-TFPI antibodies on TFPIα inhibition of FXa generation was assayed in buffer containing 50 mM HEPES, pH 7.4, 100 mM NaCl, 10 mM CaCl$_2$, 1 µg/mL BSA, 0.1% PEG8000 (w/v). Antibody (64 nM) was incubated with 4 nM TFPIα for 10 min at room temperature, before addition of a pre-incubated mixture (5 min) of FVIIa (0.5 nM) and 30 µM Dade Innovin (Dade Behring). Expression and purification of recombinant FVIIa was performed as described previously (Thim et al., 1988; Persson and Nielsen, 1996). After addition of 160 nM FX (Enzyme Research Laboratories Ltd) the reactions were incubated in a total volume of 100 ml for 30 min. The reactions were quenched by addition of 50 ml stop buffer (50 mM HEPES, pH 7.4, 100 mM NaCl, 80 mM EDTA) and the amount of FXa generated determined by addition of 50 ml of 2 mM chromogenic substrate S-2765 (Chromogenix). S-2765 cleavage was monitored at 405 nm using a Spectramax 340 Microplate spectrophotometer. The activity in the absence of TFPIα was set to 100% and the activity in the presence of TFPIα, but absence of antibody, was set to 0%. The results suggest that anti-TFPI (1-79) antibodies 2F22 and 2F3 most efficiently neutralize TFPIα inhibition of FXa generation (Table 14). As expected a TFPI KPI-2 antibody (mAb 2021 disclosed in WO2010/072691) completely neutralized TFPI inhibition.

TABLE 14

FXa activity
FXa activity generated after 30 min incubation of FVIIa, Innovin, FX and TFPI with and without antibodies. The activity in the absence of TFPIα was set to 100% and the activity in the presence of TFPIα, but absence of antibody, was set to 0%.

| Compound | FXa activity (%) |
|---|---|
| H2F22 | 40.5 |
| 2F3 | 36.6 |
| 2F45 | 21.0 |
| 2F48 | 2.9 |
| 1F56 | 18.4 |
| 1F91 | 13.9 |
| 2F35 | 18.3 |
| mAb 2021 | 103.1 |

Example 11: Effect of TFPI Antibodies Specific for TFPI (1-79) on Thromboelastography (TEG) in FVIII-Neutralised Whole Blood Citrate-stabilized whole blood was supplemented with (final concentrations): 100 µg/ml sheep anti-human FVIII antibody (Haematologic Technologies Inc., PAHFVIII-S) and 0.3 µM TF (Innovin®, 1:20,000). Clotting in the absence or presence of 100 nM TFPI antibody was initiated when 320 uL of this premix was transferred to a thromboelastograph cup containing 20 uL 0.2 M CaCl$_2$. The TEG trace was followed continuously for up to 120 min (5000 series TEG analyzer, Haemoscope Corporation, Niles, Ill., US). The following TEG variables were recorded: R time (clotting time i.e. the time from initiation of coagulation until an amplitude of 2 mm was obtained), MTG (maximal rate of thrombin generation), angle (clot development measured as the angle between the R value and the inflection point of the TEG trace) and MA (maximal amplitude of the TEG trace reflecting the maximal mechanical strength of the clot). The results show that some TFPI antibodies, but not all, shortened the clotting time (R value) and enhanced the maximal rate of thrombin generation (MTG), angle and maximal amplitude (MA) to similar extent as a reference TFPI KPI-2 antibody (mAb 2021 disclosed in WO2010/072691) (Table 15).

TABLE 15

TEG results
R time (clotting time), MTG (maximal rate of thrombin generation), Angle and MA (maximal amplitude) derived from thromboelastography curves obtained in FVIII-neutralised blood

| | R time (min) | MTG (mm * 100/sec) | Angle (°) | MA (mm) |
|---|---|---|---|---|
| FVIII neutralised blood Compound (100 nM) | | | | |
| 2021 | 6.7 | 15.8 | 55.1 | 61.8 |
| 1F91 | 8.1 | 11.4 | 47.0 | 61.2 |
| 2F3 | 7.4 | 15.1 | 54.9 | 65.6 |
| 2F22 | 6.8 | 14.2 | 56.0 | 57.0 |
| 2F35 | 12.6 | 7.7 | 35.7 | 69.6 |
| 2F45 | 7.5 | 13.5 | 50.9 | 63.5 |
| — | 17.1 | 6.9 | 29.6 | 67.2 |
| Normal blood | 6.1 | 19.3 | 60.3 | 65.6 |

While certain features of the invention have been illustrated and described herein many modifications, substitutions, changes, and equivalents will now occur to those of ordinary skill in the art. It is, therefore, to be understood that the appended claims are intended to cover all such modifications and changes, as fall within the true spirit of the invention.

The invention claimed is:

1. An isolated antibody or fragment thereof comprising: said antibody or fragment thereof which specifically binds to an epitope present in amino acid residues 1 to 79 of human TFPI (SEQ ID NO: 2) comprising a heavy chain and a light chain, wherein,
the heavy chain comprises:
 a CDR1 sequence corresponding to amino acids 31 to 35 of SEQ ID NO: 6 (NYGVH),
 a CDR2 sequence corresponding to amino acids 50 to 65 of SEQ ID NO: 6 (VIWRGGSIDYNAAFMS), and
 a CDR3 sequence corresponding to amino acids 98 to 110 of SEQ ID NO: 6 (NSHGNYVGYAMDY); and
the light chain comprises:
 a CDR1 sequence corresponding to amino acids 24 to 34 of SEQ ID NO: 7 (KASQSVGPAVA),
 a CDR2 sequence corresponding to amino acids 50 to 56 of SEQ ID NO: 7 (SASNRYT), and
 a CDR3 sequence corresponding to amino acids 89 to 96 of SEQ ID NO: 7 (QQYTSYPT).

2. The antibody or fragment thereof according to claim 1, which specifically binds an epitope present in amino acid residues 26 to 76 (KPI-1) of human TFPI (SEQ ID NO: 2).

3. The antibody or fragment thereof according to claim 1, which specifically binds an epitope present in human TFPI wherein said epitope comprises at least one of the following amino acid residues L16, P17, L19, K20, L21, M22, F25, C35, A37, M39, R41, Y56, G57, G58, C59, E60, G61, N62, Q63, R65, F66, E67, E71 and M75 of SEQ ID NO: 2.

4. The antibody or fragment thereof according to claim 3, which specifically binds an epitope present in human TFPI wherein said epitope comprises at least one of the following amino acid residues R41, R65 and E67 of SEQ ID NO: 2.

5. The antibody or fragment thereof according to claim 1, which has a $K_d$ equal to or less than 1E-08 M, as determined using surface plasmon resonance.

6. A pharmaceutical formulation comprising an isolated antibody or fragment thereof according to claim 1 and at least one pharmaceutically acceptable excipient.

7. A method of treating a subject in need thereof comprising administering a pharmaceutical formulation according to claim 6 to said subject, wherein said subject has a congenital, acquired and/or iatrogenic coagulopathy.

8. The method according to claim 7, wherein said subject has haemophilia A with inhibitors, haemophilia A without inhibitors, haemophilia B with inhibitors, or haemophilia B without inhibitors.

9. A method of treating a subject in need thereof comprising administering the antibody or fragment thereof according to claim 1 to said subject, wherein said subject has a congenital, acquired and/or iatrogenic coagulopathy.

10. The method according to claim 9, wherein said subject has haemophilia A with inhibitors, haemophilia A without inhibitors, haemophilia B with inhibitors, or haemophilia B without inhibitors.

* * * * *